US009993592B2

(12) United States Patent
Amirouche et al.

(10) Patent No.: US 9,993,592 B2
(45) Date of Patent: *Jun. 12, 2018

(54) CARTRIDGE SYSTEM FOR DELIVERY OF MEDICAMENT

(71) Applicant: PICOLIFE TECHNOLOGIES, LLC, Deerfield, IL (US)

(72) Inventors: Farid Amirouche, Highland Park, IL (US); Arash N. Attar, Chicago, IL (US); Matthew L. Cantwell, Northbrook, IL (US)

(73) Assignee: Picolife Technologies, LLC, Jacksonville, FL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/288,052

(22) Filed: May 27, 2014

(65) Prior Publication Data

US 2014/0257350 A1    Sep. 11, 2014

Related U.S. Application Data

(63) Continuation of application No. 13/308,899, filed on Dec. 1, 2011, now Pat. No. 8,771,229.

(51) Int. Cl.
*A61M 5/14* (2006.01)
*A61M 5/168* (2006.01)
*A61M 5/142* (2006.01)

(52) U.S. Cl.
CPC ........ *A61M 5/1413* (2013.01); *A61M 5/1422* (2013.01); *A61M 5/14224* (2013.01); *A61M 5/16827* (2013.01); *A61M 2205/12* (2013.01)

(58) Field of Classification Search
CPC ............ A61M 5/1413; A61M 5/14224; A61M 5/1422; A61M 5/16827; A61M 2205/12
See application file for complete search history.

(56) References Cited

U.S. PATENT DOCUMENTS

| | | |
|---|---|---|
| 2,398,435 A | 4/1946 | Marks |
| 3,137,242 A | 6/1964 | Hahn |
| 3,498,228 A | 3/1970 | Blumle et al. |
| 3,691,263 A | 9/1972 | Stoy et al. |

(Continued)

FOREIGN PATENT DOCUMENTS

| | | |
|---|---|---|
| EA | 0 024 431 B1 | 8/1985 |
| EP | 0 299 628 A1 | 1/1989 |

(Continued)

OTHER PUBLICATIONS

International Search Report and Written Opinion issued in International Patent Application No. PCT/US2013/072787, dated Apr. 24, 2014 (9 pages).

(Continued)

*Primary Examiner* — Theodore Stigell
(74) *Attorney, Agent, or Firm* — Ashkan Najafi

(57) ABSTRACT

A cartridge system for delivery of medicament includes as membrane placed between two disk magnets that are housed within pump body inserts. The pump body inserts having flow channels and fluid openings are between two inlet/outlet members. The inlet/outlet members each having a fluid outlet component and fluid openings are securely engaged to two reservoirs containing fluid medicaments.

14 Claims, 37 Drawing Sheets

(56) References Cited

U.S. PATENT DOCUMENTS

| | | |
|---|---|---|
| 3,771,694 A | 11/1973 | Kaminski |
| 3,827,565 A | 8/1974 | Matsumura |
| 3,889,710 A | 6/1975 | Brost |
| 3,915,609 A | 10/1975 | Robinson |
| 4,017,238 A | 4/1977 | Robinson |
| 4,197,266 A | 4/1980 | Clark et al. |
| 4,257,416 A | 3/1981 | Prager |
| 4,340,048 A | 7/1982 | Eckenhoff |
| 4,376,618 A | 3/1983 | Toyoda et al. |
| 4,415,003 A | 11/1983 | Paradis et al. |
| 4,498,843 A | 2/1985 | Schneider et al. |
| 4,544,369 A | 10/1985 | Skakoon et al. |
| 4,552,561 A | 11/1985 | Eckenhoff et al. |
| 4,657,486 A | 4/1987 | Stempfle et al. |
| 4,712,583 A | 12/1987 | Pelmulder et al. |
| 4,731,726 A | 3/1988 | Allen, III |
| 4,784,644 A | 11/1988 | Sawyer et al. |
| 4,797,144 A | 1/1989 | DeMeritt et al. |
| 4,840,754 A | 6/1989 | Brown et al. |
| 4,936,833 A | 6/1990 | Sams |
| 4,938,742 A | 7/1990 | Smits |
| 4,946,448 A | 8/1990 | Richmond |
| 4,947,856 A | 8/1990 | Beard |
| 4,958,661 A | 9/1990 | Holtermann et al. |
| 4,966,199 A | 10/1990 | Ruschke |
| 5,019,974 A | 5/1991 | Beckers |
| 5,050,612 A | 9/1991 | Matsumura |
| 5,147,323 A | 9/1992 | Haber et al. |
| 5,218,993 A | 6/1993 | Steinberg et al. |
| 5,246,634 A | 9/1993 | Ichikawa et al. |
| 5,370,635 A | 12/1994 | Strausak et al. |
| 5,584,815 A | 12/1996 | Pawelka et al. |
| 5,645,855 A | 7/1997 | Lorenz |
| 5,674,557 A | 10/1997 | Wildman et al. |
| 5,709,662 A | 1/1998 | Olive et al. |
| 5,762,632 A | 6/1998 | Whisson |
| 5,775,671 A | 7/1998 | Cote, Sr. |
| 5,822,715 A | 10/1998 | Worthington et al. |
| 5,858,001 A | 1/1999 | Tsals et al. |
| 6,003,736 A | 12/1999 | Ljunggren |
| 6,017,331 A | 1/2000 | Watts et al. |
| 6,056,718 A | 5/2000 | Funderburk et al. |
| 6,305,661 B1 | 10/2001 | Kennedy |
| 6,311,712 B1 | 11/2001 | Meyer |
| 6,315,929 B1 | 11/2001 | Ishihara et al. |
| 6,390,120 B1 | 5/2002 | Guala |
| 6,409,707 B1 | 6/2002 | Guala |
| 6,572,586 B1 | 6/2003 | Wojcik |
| 6,627,124 B1 | 9/2003 | Herbrechtsmeier et al. |
| 6,648,859 B2 | 11/2003 | Bitdinger et al. |
| 6,723,086 B2 | 4/2004 | Bassuk et al. |
| 6,813,906 B1 | 11/2004 | Hirota et al. |
| 6,945,963 B2 | 9/2005 | Langley et al. |
| 7,044,125 B2 | 5/2006 | Vedrine et al. |
| 7,061,108 B2 | 6/2006 | Wright et al. |
| 7,104,973 B2 | 9/2006 | Woolston et al. |
| 7,123,985 B2 | 10/2006 | Wildsmith et al. |
| 7,296,782 B2 | 11/2007 | Enerson et al. |
| 7,302,311 B2 | 11/2007 | Varis |
| 7,407,490 B2 | 8/2008 | Bendsen et al. |
| 7,470,265 B2 | 12/2008 | Massengale |
| 7,510,544 B2 | 3/2009 | Vilks et al. |
| 7,537,590 B2 | 5/2009 | Santini, Jr. et al. |
| 7,585,167 B2 | 9/2009 | Lawton et al. |
| 7,637,899 B2 | 12/2009 | Woolston et al. |
| 7,846,146 B2 | 12/2010 | Woolston et al. |
| 7,850,663 B2 | 12/2010 | Sullivan et al. |
| 7,896,002 B2 | 3/2011 | Watanabe |
| 7,914,499 B2 | 3/2011 | Gonnelli et al. |
| 7,935,280 B2 | 5/2011 | Lawton et al. |
| 7,967,795 B1 | 6/2011 | Cabiri |
| 8,021,334 B2 | 9/2011 | Shekalim |
| 8,663,538 B2 | 3/2014 | Amirouche et al. |
| 8,764,425 B2 | 7/2014 | Amirouche et al. |
| 8,771,229 B2* | 7/2014 | Amirouche ......... A61M 5/1422 417/477.2 |
| 8,790,307 B2* | 7/2014 | Amirouche ......... A61M 5/1413 604/151 |
| 8,807,169 B2 | 8/2014 | Amirouche et al. |
| 2002/0119711 A1 | 8/2002 | VanAntwerp et al. |
| 2003/0100883 A1 | 5/2003 | Kristensen et al. |
| 2003/0180164 A1 | 9/2003 | Bunner et al. |
| 2004/0050104 A1 | 3/2004 | Ghosh et al. |
| 2004/0176727 A1 | 9/2004 | Shekalim |
| 2005/0065500 A1 | 3/2005 | Couvillon, Jr. et al. |
| 2005/0192557 A1 | 9/2005 | Brauker et al. |
| 2006/0021386 A1 | 2/2006 | Wang |
| 2006/0073232 A1 | 4/2006 | Wang |
| 2006/0145372 A1 | 7/2006 | Jones et al. |
| 2006/0224109 A1 | 10/2006 | Steil et al. |
| 2007/0073230 A1 | 3/2007 | Jasperson et al. |
| 2007/0087068 A1 | 4/2007 | Eiha et al. |
| 2007/0225147 A1 | 9/2007 | Hayashi et al. |
| 2007/0233008 A1 | 10/2007 | Kristensen et al. |
| 2007/0299398 A1 | 12/2007 | Alferness et al. |
| 2008/0169444 A1 | 7/2008 | Guala |
| 2009/0062767 A1 | 3/2009 | Van Antwerp et al. |
| 2009/0069650 A1 | 3/2009 | Jennewine |
| 2009/0105658 A1 | 4/2009 | Jennewine |
| 2010/0004603 A1 | 1/2010 | Kristensen et al. |
| 2010/0081993 A1 | 4/2010 | O'Connor |
| 2010/0100077 A1 | 4/2010 | Rush et al. |
| 2010/0185322 A1 | 7/2010 | Bylsma et al. |
| 2010/0225013 A1 | 9/2010 | Eiha et al. |
| 2010/0241086 A1 | 9/2010 | Yodfat et al. |
| 2010/0255366 A1 | 10/2010 | Myland |
| 2010/0256593 A1 | 10/2010 | Yodfat et al. |
| 2010/0280461 A1 | 11/2010 | Forstreuter |
| 2010/0317093 A1 | 12/2010 | Turewicz et al. |
| 2011/0021905 A1 | 1/2011 | Patrick et al. |
| 2011/0066131 A1 | 3/2011 | Cabiri |
| 2011/0114744 A1 | 5/2011 | Ricciardi et al. |
| 2011/0118675 A1 | 5/2011 | Miller et al. |
| 2011/0137287 A1 | 6/2011 | Gonnelli et al. |
| 2011/0160696 A1 | 6/2011 | Hoss |
| 2011/0168294 A1 | 7/2011 | Jakobsen et al. |
| 2011/0251546 A1 | 10/2011 | Sullivan et al. |
| 2011/0274566 A1* | 11/2011 | Amirouche ......... A61M 5/14224 417/322 |
| 2011/0308650 A1 | 12/2011 | Amirouche et al. |
| 2011/0309229 A1 | 12/2011 | Amirouche et al. |
| 2011/0309552 A1 | 12/2011 | Amirouche et al. |
| 2012/0002422 A1 | 1/2012 | Lia et al. |
| 2012/0053571 A1 | 3/2012 | Petri |
| 2013/0144254 A1 | 6/2013 | Amirouche et al. |
| 2013/0237947 A1 | 9/2013 | Amirouche et al. |
| 2013/0274576 A1 | 10/2013 | Amirouche et al. |
| 2013/0274577 A1 | 10/2013 | Amirouche et al. |
| 2013/0345650 A1 | 12/2013 | Amirouche |
| 2014/0155819 A1 | 6/2014 | Amirouche et al. |

FOREIGN PATENT DOCUMENTS

| | | |
|---|---|---|
| GB | 2 248 891 A | 4/1992 |
| JP | 62-297120 A | 12/1987 |
| JP | 2007-015906 A | 1/2007 |
| JP | 2007-0119280 A | 5/2007 |
| JP | 2008-96089 A | 4/2008 |
| WO | WO 03/047426 A1 | 6/2003 |
| WO | WO 2004/067964 A | 8/2004 |
| WO | WO 2006/111775 A | 10/2006 |
| WO | WO 2007/055642 A1 | 5/2007 |
| WO | 20 2009/048462 A1 | 4/2009 |
| WO | WO 2010/128914 A1 | 11/2010 |

OTHER PUBLICATIONS

U.S. Appl. No. 13/174,598, filed Jun. 30, 2011, by Amirouche et al.: Notice of Allowance, dated Apr. 7, 2014.

U.S. Appl. No. 13/174,624, filed Jun. 30, 2011 by Amirouche et al.: Notice of Allowance, dated Feb. 5, 2014.

(56) References Cited

OTHER PUBLICATIONS

U.S. Appl. No. 13/308,899, filed Dec. 1, 2011, by Amirouche et al.: Notice of Allowance, dated Feb. 28, 2014.
U.S. Appl. No. 13/370,091, filed Feb. 9, 2012, by Amirouche et al.: Notice of Allowance, dated Mar. 25, 2014.
"Bartels micropumps," Apr. 2009, [online] http://www.bartelsmikrotechnik.de/index.php/micropumps.html.
"Diabetes Basics: Diabetes Statistics," American Diabetes Association, [Online]. Available at: http://www.diabetes.org/diabetes-basics/. [Accessed May 14, 2012] (3 pages).
"Diabetic Neuropathy, Living With Numbness and Pain," A Diabetic Life, [Online]. Available at: http://www.a-diabetic-life.com/diabetic-neuropathy.html. [Accessed May 5, 2012] (3 pages).
"Electromyogram (EMG)," MedicineNet.com, [Online]. Available at: http://www.medicinenet.com/electromyogram/article.htm. [Accessed May 15, 2012] (3 pages).
"Nerve conduction velocity," MedlinePlus®, A Service of the U.S. National Library of Medicine, National Institutes of Health, [Online]. Available at: http://www.nlm.nih.gov/medlineplus/ency/article/003927.htm; updated Jun. 18, 2011 (3 pages).
"Peripheral Neuropathy Fact Sheet," National Institue of Neurological Disorders and Stroke, NIH Publication No. 04-4853, [Online]. Available: http://www.ninds.nih.gov/disorders/peripheralneuropathy/detail_peripheralneuropathy.htm; updated Sep. 19, 2012 (9 pages).
"Peripheral Neuropathy Market Approaches US$1B by 2012," PR Newswire, United Business Media [Online]. Available at: http://www.prnewswire.co.uk/news-releases/peripheral-neuropathymarket-approaches-us1b-by-2012-154534705.html. Apr. 7, 2012 (2 pages).
"Silastic® BioMedical Grade ETR elastomers", Dow Corning, 2002-2011, accessed at http://www4.downcorning.com/DataFiles/090007c88028669a.pdf (5 pages).
"Silastic® Biomedical Grade Liquid Silicone Rubers", Down Corning, 2006, accessed at http://www4.dowcorning.com/DataFiles/090007c88097f96.pdf (6 pages).
"Small, powerful, light, precise: micro diaphragm pumps made of plastics: thinXXS micropumps" Mar. 2009, [online] http://www.thinxxs.com/main/produkte/micropumps.html (2 pages).
"*Sylgard*® 164 Silicone Elastomer", Dow Corning, 2007, accessed at http://ncnc.engineering.ucdavis.edu/pages/equipment/Sylgard_164_data_sheet.pdf (3 pages).
Acevedo, "Creation of Dual Chamber Micropump Using Rapid Prototyping," Milwaukee School of Engineering, Research Experience for Undergraduates Paper, 2005. Available online at: http://www.msoe.edu/academics/research_centers/reu/pdf/2005/Creation%20of%20a%20Dual%20Chamber%20Micropump%20using%20Rapid%20Prototyping.pdf (6 pages).
Amirouche et al., "Current Micropump Technologies and Their Biomedical Applications," Microsystem Technology, 2009, pp. 647-666, vol. 15.
Anhalt et al., "Insulin Patch Pumps: Their Development and Future in Closed-Loop Systems," *Diabetes Technology & Therapeutics*, 2010, pp. 51-58, vol. 12.
Bak et al., "Multiple Insulin Injections Using a Pen Injector Versus Insulin Pump Treatment in Young Diabetic Patients," Diabetes Research, 1987, pp. 155-158, vol. 6.
Barbano et al., "Effectiveness, Tolerability, and Impact on Quality of Life of the 5% Lidocaine Patch in Diabetic Polyneuropathy," Archives of Neurology, 2004, pp. 914-918, vol. 61, No. 6.
Bohm et al., "A plastic micropump constructed with conventional techniques and materials," Sensors and Actuators A, vol. 77-3, pp. 223-228, 1999.
Casella et al., "Accuracy and Precision of Low-Dose Insulin Administration," Pediatrics, 1993, pp. 1155-1157, vol. 91.
Dario et al., "A fluid handling system for a chemical microanalyzer," J. Micromech. Microeng., vol. 6, pp. 95-98, 1996.
Davis et al., "Techniques for Improved Soft Lens Fitting"; Aug. 1, 2005, p. 2, accessed at http://www.cispectrum.com/articleviewer.aspx?articleid=12852 (5 pages).

Einhorn et al., "Advances in Diabetes for the Millennium: Insulin Treatment and Glucose Monitoring," Medscape General Medicine, 2004, p. 8, vol. 6, (3 Suppl.) [Online]. Available at: http://www.medscape.org/viewarticle/488996 (9 pages).
Elleri et al., "Closed-Loop Insulin Delivery for Treatment of Type 1 Diabetes," BMC Medical, 2011, p. 120, vol. 9 [Online]. Available at: http://www.biomedcentral.com/1741-7015/9/120 (9 pages).
Farnbach, "Peripheral Nerve Testing and Electromyography," [Online]. Available at: http://cal.vet.upenn.edu/projects/saortho/appendix_d/appd.htm. [Accessed May 18, 2012] (10 pages).
Fu et al. "TiNi-based thin films in MEMS applications: a review," Sensors and Actuators A, 2004, pp. 3950408, vol. 112, No. 23.
Galer et al., "The Lidocaine Patch 5% Effectively Treats All Neuropathic Pain Qualities: Results of a Randomized, Double-Blind, Vehicle-Controlled, 3-Week Efficacy Study with Use of the Neuropathic Pain Scale," The Clinical Journal of Pain, 2002, pp. 297-301, vol. 18, No. 5 (Abstract).
Gammaitoni et al., "Pharmacokinetics and Tolerability of Lidocaine Patch 5% with Extended Dosing," The Annals of Pharmacotherapy, 2002, pp. 236-240, vol. 36, No. 2, (Abstract).
Ha et al., "Disposable thermo-pneumatic micropump for bio lab-on-a-chip application," Microelectronic Engineering, 2009, pp. 1337-1339, vol. 86.
Ignaut et al., "Comparative Device Assessments: Humalog KwikPen Compared with Vial and Syringe and FlexPen," The Diabetes Educator, 2009, pp. 789-798, vol. 35, No. 2.
International Search Report and Written Opinion issued in International Patent Application No. PCT/US2009/059020, dated Mar. 9, 2010 (17 pages).
International Search Report and Written Opinion issued in PCT International Application No. PCT/US2012/066937, dated Mar. 7, 2013 (9 pages).
International Search Report and Written Opinion issued in International Patent Application No. PCT/US2013/035918, dated Jun. 21, 2013 (9 pages).
International Search Report and Written Opinion issued in International Patent Application No. PCT/US2013/035921, dated Jul. 1, 2013 (11 pages).
International Search Report and Written Opinion issued in International Patent Application No. PCT/US0213/046546, dated Aug. 8, 2013 (11 pages).
Irawan et al., "Fabrication and performance testing of disposable micropump suitable for microfluidic chip," in Intl. Conf. on Biomedical and Pharmaceutical Engineering, Orchard Hotel, Singapore, Dec. 2006, 252-255.
Jeong, et al. "Fabrication of a peristaltic PDMS micropump," Sensors and Actuators A, vol. 123-124, pp. 453-458, 2005.
Junwu et al., "Design and test of a high-performance piezoelectric micropump for drug delivery," Sensors and Actuators A, vol. 121, pp. 156-161, 2005.
Klonoff et al., "Insulin Pump Safety Meeting: Summary Report," Journal of Diabetes Science and Technology, 2009, pp. 396,402, vol. 3, No. 2.
Koch, et al., "PDMS and tubing-based peristaltic micropumps with direct actuation," Sensors and Actuators B, vol. 135, pp. 664-670, 2009.
Laser et al., "A review of micropumps," J. Micromech. Microeng., vol. 14(6), pp. R35-R64, 2004.
Lee et al., "Microfluidic mixing: A review," Int. J. Mol. Sci., 2011, pp. 3263-3287, vol. 12.
Li et al., "A high frequency high flow rate piezoelectrically driven MEMS micropump" in Proceedings IEEE Solid State Sensors and Actuators Workshop, Hilton Head, SC, Jun. 2000 (4 pages).
Ma et al., "Development and application of a diaphragm micropump with piezoelectric device," Microsyst. Technol., vol. 14, pp. 1001-1007, 2008.
Manz, et al., "Miniaturized total chemical analysis systems: a novel concept for chemical sensing," Sensors and Actuators B, vol. 1, pp. 244-248, 1990.
Meece et al., "Effect of Insulin Pen Devices on the Management of Diabetes Mellitus," Am J Health-Syst. Pharm., 2008, pp. 1076-1082, vol. 65.

(56) References Cited

OTHER PUBLICATIONS

Melin et al., "A fast passive and planar liquid sample micromixer," Lab on a Chip, 2004, pp. 214-219, vol. 4.
Morrow, "Transdermal Patches Are More Than Skin Deep," Managed Care [Online]. Available at: http://www.managedcaremag.com/archives/0404/0404.biotech.html. Apr. 2004 (4 pages).
Mundell, "Antidepressant Cymbalta Might Ease Chemo-Linked Pain," MSN Healthy Living, 2013 [Online]. Available at: http://health.msn.com/health-topics/cancer/antidepressant-cymbalta-might-ease-chemo-linked-pain (4 pages).
Nguyen et al., "MEMS-micropumps: A review," Journal of Fluids Engineering, vol. 124, p. 384-392, 2002.
Nguyen et al., "Microfluidics for Internal Flow Control: Micropumps," in *Fundamentals and Applications of Microfluidics*. Norwood, MA: Artech House, Inc., 2002; pp. 293-341.
Nisar et al., "MEMS-based Micropumps in Drug Delivery and Biomedical Applications," Sensors and Actuators B, 2006, pp. 917-942, vol. 130.
Pallikaris, "Intracorneal mico-lens a minimally invasive option for presbyopia"; Aug. 10, 2010, p. 1, paragraph 003, accessed at http://www.rigneygraphics.com/clients/presbia/website/newsmedia/pdfs/press-osn-presbia.pdf (2 pages).
Pan et al., "A magnetically driven PDMS micropump with ball check-valves," J. Micromech. Microeng. vol. 15, pp. 1021-1026, 2005.
Rapp et al., "Liga micropump for gases and liquids," Sensors and Actuators A, 1994, pp. 57-61, vol. 40, No. 1.
Richardson et al., "Peripheral Neuropathy: A True Risk Factor for Falls," The Journal of Gerontology: Series A, 1995, pp. 211-215, vol. 50, No. 4 (Abstract).
Roberts, "Blind Attack on Wireless Insulin Pumps Could Deliver Lethal Dose," Threatpost.com, The Kaspersky Lab Security News Service, Oct. 27, 2011 (2 pages).
Rosielle, "The Lidocaine Patch," Medical College of Wisconsin [Online]. Available: http://www.eperc.mcw.edu/EPERC/FastFactsindex/ff_146.htm. [Accessed May 15, 2012] (3 pages).
Santra et al., "Fabrication and testing of a magnetically actuated micropump," Sensors and Actuators B, vol. 87, pp. 356-364, 2002.
Selam, "Evolution of Diabetes Insulin Delivery Devices," Journal of Diabetes Science and Technology, 2010, pp. 505-513, vol. 4, No. 3.
Shen et al., "Miniaturized PMMA ball-valve with micropump with cylindrical electromagnetic actuator," Microelectronic Engineering, vol. 85, pp. 1104-1107, 2008.
Singhal, et al., "Microscale pumping technologies for microchannel cooling systems," Appl. Mech. Rev., vol. 57(3), pp. 191-221, 2004.

Star Micronics Co. Ltd., "Precision products," Mar. 2009, [online]. Accessed at: http://www.star-m.jp/eng/products/precision/index/html, on Aug. 22, 2011 (4 pages).
Trenkle et al., "Normally-closed peristaltic micropump with re-usable actuator and disposable fluidic chip," Sensors and Actuators B, vol. 154, pp. 137-141, 2011.
Tsai et al., "Review of MEMS-based drug delivery and dosing systems," Sensors and Actuators A, vol. 134, No. 2, pp. 555-564, 2007.
U.S. Appl. No. 13/174,598, filed Jun. 30, 2011, by Amirouche et al.: Non-Final Rejection, dated May 14, 2013.
U.S. Appl. No. 13/174,598, filed Jun. 30, 2011, by Amirouche et al.: Final Rejection, dated Oct. 3, 2013.
U.S. Appl. No. 13/174,624, filed Jun. 30, 2011 by Amirouche et al.: Non-Final Rejection, dated Jun. 28, 2012.
U.S. Appl. No. 13/174,624, filed Jun. 30, 2011 by Amirouche et al.: Final Rejection, dated Nov. 21, 2012.
U.S. Appl. No. 13/174,624, filed Jun. 30, 2011 by Amirouche et al.: Non-Final Rejection, dated Feb. 8, 2013.
U.S. Appl. No. 13/174,624, filed Jun. 30, 2011 by Amirouche et al.: Final Rejection, dated Jul. 31, 2013.
U.S. Appl. No. 13/174,643, filed Jun. 30, 2011 by Amirouche et al.: Non-Final Rejection, dated May 2, 2013.
U.S. Appl. No. 13/174,643, filed Jun. 30, 2011 by Amirouche et al.: Notice of Allowance, dated Oct. 21, 2013.
U.S. Appl. No. 13/308,899, filed Dec. 1, 2011 by Amirouche et al.: Non-Final Rejection, dated Aug. 8, 2013.
U.S. Appl. No. 13/370,091, filed Feb. 9, 2012, by Amirouche et al.: Non-Final Rejection, dated Aug. 21, 2013.
U.S. Appl. No. 13/649,202, filed Oct. 11, 2012, by Amirouche: Non-Final Rejection, dated Jun. 18, 2013.
U.S. Appl. No. 13/649,202, filed Oct. 11, 2012, by Amirouche: Final Rejection, dated Jan. 20, 2014.
U.S. Appl. No. 13/692,868, filed Dec. 3, 2012, by Amirouche et al.
Van Lintel, et al., "A piezoelectric micropump based on micromachining of silicon," Sensors and Actuators A, vol. 15, 153-167, 1988.
Yadav et al., "Various Non-Injectable Delivery Systems for the Treatment of Diabetes Mellitus," Endocrine, Metabolic & Immune Disorders-Drug Targets, 2009, pp. 1-13, vol. 9, No. 1.
Yamahata, et al. "A PMMA valveless micropump using electromagnetic actuation." Microfluid Nanofluid, vol. 1, pp. 197-207, 2005.
Zhu et al., "Optimization design of multi-material micropump using finite element method," Sensors and Actuators A, vol. 149, pp. 130-135, 2009.

\* cited by examiner

CARTRIDGE SYSTEM FOR DELIVERY OF MEDICAMENT

CROSS-REFERENCE TO RELATED APPLICATION

This application is a continuation of and claims priority to U.S. Nonprovisional Patent Application Ser. No. 13/308,899, filed Dec. 1, 2011 (now U.S. Pat. No. 8,771,229, granted Jul. 8, 2014), and titled "CARTRIDGE SYSTEM FOR DELIVERY OF MEDICAMENT", the entire contents of which are incorporated herein by reference.

BACKGROUND OF THE INVENTION

1. Field of the Invention:

The present invention relates to the field of medical devices and, in particular, to devices for delivery of medicament. More particularly, the present invention relates to a cartridge system for delivery of insulin or other medicament.

2. Description of the Related Art:

Diabetes is a disease caused by the body's failure to produce adequate insulin or the cell's failure to respond to insulin resulting in high levels of sugar in the blood. If left untreated, diabetes can cause numerous complications. Typically, treatment for diabetes required both repeated checking of blood glucose levels and several injections of insulin throughout the day. Major drawbacks of such treatment were the need to draw blood and test glucose levels throughout the day, improper or low dosage amounts of insulin, contamination of the insulin delivery system, or lifestyle restriction. Low dosages of insulin over an extended period may cause heart disease, stroke, kidney failure, hypertension, or retinal damage.

Diabetes may be controlled by insulin replacement therapy in which insulin is delivered to the diabetic person, usually by injection, to counteract elevated blood glucose levels. Recent therapies include the basal/bolus method of treatment in which basal, a long acting insulin medication, for example, Humalog® and Apidra®, is delivered via injection once every day. The basal provides the body with a relatively constant dose of insulin throughout the day. At mealtime, an additional dose of insulin, or bolus, is administered based on the amount of carbohydrate and protein in the meal. Accurate calculations of various parameters including the amount of carbohydrates and proteins consumed, and the lapse in time since the last dosage are necessary to determine the appropriate dosage of insulin. The dosages are thus prone to human error and the method is ineffective when doses are skipped, forgotten or miscalculated. Exercise, stress and other factors can also cause the calculations to be inaccurate.

To address these problems, programmable insulin delivery devices or pumps were developed which seek to mimic the way a normal, healthy pancreas delivers insulin to the body. Insulin pumps are programmed to deliver a continual basal dose of insulin and occasionally a bolus dose in response to a patient's meal intake and physical activities. Additionally, the number of times a patient is required to draw blood and test their glucose during the day is reduced, thus lessening the pain and inconvenience of this disease.

Conventional insulin pumps are worn on the body and are connected to a patient via a cannula that is inserted somewhere on the patient's abdomen. The insulin is delivered under the skin and is absorbed into the body through the subcutaneous fat layer. Insulin pumps in the past have been quite large, some requiring the use of a shoulder bag to transport. Over time, they have become smaller in size and most pumps today are roughly the size of a deck of cards. Currently available insulin pumps include Animas OneTouch®Ping®, Deltec Cozmo®, Disetronic Accu-Chek Spirit®, Insulet OmniPod, Medtronic Paradigm™, Sooil USA DiabecareII, and Nipro Amigo®.

With the decreased size of the pump unit also comes a decreased size in the medication reservoir. This reduced reservoir size means more frequent refilling, greater potential for contamination of the reservoir, more frequent changes of the cannula and tubing, and greater expense overall in treating the condition. Recent medical data suggests that a combination of insulin and another medication, such as glucagon, infused at different times or simultaneously, leads to better results in patients.

Therefore, the need exists for a low-cost cartridge system, capable of working in tandem with a pump driver system, that contains a plurality of reservoirs for the delivery of more than one drug.

SUMMARY OF THE INVENTION

The present invention overcomes the disadvantages of the prior art and fulfills the needs noted above by providing a drug delivery device having a pump driver system, and a cartridge system.

More specifically, the present invention includes a cartridge system having a plurality of reservoirs each with volume, preferably, of 1.5 ml. Each of the plurality of reservoirs can be pre-filled with different medicaments. A pump membrane is placed between two gold-plated neodymium-iron-boron disk magnets that are each housed within a pump body insert. Each of the pump body inserts has a fluid receiving opening, a fluid discharge opening, a plurality of inlet channels, and a plurality of outlet channels. The pump body inserts are placed between two inlet/outlet members. Each of the inlet/outlet members has a fluid receiving opening, a fluid discharge opening, and a fluid outlet component. Additionally, each of the inlet/outlet members has a male part that securely engages to a female part of the reservoir forming an airtight seal. The reservoir, the fluid receiving opening of the inlet/outlet member, the fluid receiving opening, the plurality of inlet channels, the plurality of outlet channels, and the fluid discharge opening of the pump body insert, the fluid discharge opening and the fluid outlet component of the inlet/outlet member are in fluid communication. The cartridge system further includes valve membranes that are placed between the fluid receiving openings of the pump body inserts and the inlet/outlet members, and between the fluid discharge openings of the pump body inserts and the inlet/outlet members.

The valve membranes of the cartridge system can be pre-stressed and formed, for example, of Silastic Q7-4840. The reservoirs can be formed, for example, of Silastic Q7-4840, or Medical Grade Polyisoprene. The pump body inserts and the inlet/outlet members can be formed, for example, of clear polypropylene homopolymer. The pump membrane can be formed, for example, of Silastic Q7-4840.

The present invention also includes a cartridge system having a plurality of orifices to fill or re-fill a plurality of medicaments in the reservoirs. The plurality of orifices can be located on the reservoirs, or on the inlet/outlet members and the plurality of orifices are in fluid communication with the reservoirs.

The present invention further includes a method of delivering medicament using a drug delivery device having a cartridge system. The method includes the steps of providing a drug delivery device having a pump driver system and a cartridge system, loading a plurality of pre-filled reservoirs containing fluid medicament to the cartridge system, engaging securely the cartridge system and the pump driver system, selecting various parameters on a user interface of the pump driver system including selecting pre-determined values or specifying user-defined values for the parameters, and connecting an infusion set to the drug delivery device.

The method of delivering medicament using the drug delivery device includes the additional steps of placing an inset of the infusion set on a body part of a patient, attaching the infusion set to the patient's body, and switching on the drug delivery device.

The method of delivering medicament using the drug delivery device wherein the step of connecting an infusion set to the drug delivery device further includes the steps of connecting one end of a Y-catheter to an outlet component of an inlet/outlet member, and delivering fluid medicament at a given rate. The step of delivering fluid medicament at a given rate can further include delivering fluid medicament at a controlled and continuous rate for a pre-determined or user-defined period of time. Alternatively, the step of delivering fluid medicament at a given rate can further include delivering fluid medicament at a programmable rate that is regulated by the patient.

The present invention also includes a method of delivering medicament using the drug delivery device having the cartridge system. The method includes the steps of providing a drug delivery device having a pump driver system and a cartridge system, loading a plurality of reservoirs to the cartridge system, using an instrument to inject a plurality of fluid medicaments into the plurality of reservoirs, engaging securely the cartridge system and the pump driver system, selecting various parameters on a user interface of the pump driver system including selecting pre-determined values or specifying user-defined values for the parameters, and connecting an infusion set to the drug delivery device. The step of connecting an infusion set to the drug delivery device further includes the steps of connecting one end of a Y-catheter to an outlet component of an inlet/outlet member, and delivering fluid medicament at a given rate. The step of delivering fluid medicament at a given rate can further include delivering fluid medicament at a controlled and continuous rate for a pre-determined or user-defined period of time. Alternatively, the step of delivering fluid medicament at a given rate can further include delivering fluid medicament at a programmable rate that is regulated by the patient.

The present invention further includes a drug delivery device having a pump driver system, a cartridge system, a cannula and an insertion mechanism, and a plurality of conduits. The pump driver system includes a driver that drives the magnets that applies a force to the pump membrane of the cartridge system, a controller in communication with the pump to adjust the force applied by the driver, a power source, and a user interface configured to present information to a user. The cartridge system of the device snaps into the pump driver system and is securely engaged to it. The plurality of conduits each includes a proximal end, a distal end, and a lumen extending from its proximal end to its distal end. The proximal ends of the plurality of conduits are securely engaged to the distal ends of the cannula and the insertion mechanism, and the distal ends are securely engaged to the proximal ends of the fluid outlet component of the inlet/outlet members of the cartridge system.

Other features and advantages of the present invention will become apparent from the following description of the invention, which refers to the accompanying drawings.

DETAILED DESCRIPTION OF THE PREFERRED EMBODIMENTS

Disclosed embodiments relate to a cartridge system for delivery of medicament and a drug delivery device containing the same.

The term "fluid" is defined as a state of matter or substance (liquid or gas) whose particles can move about freely, and has no fixed shape or conform to the shape of their containers.

The term "channel" is defined as a passage for fluids to flow through.

The term "medicament" is defined as a substance used in therapy, a substance that treats, prevents or alleviates the symptoms of disease, a medicine in a specified formulation, or an agent that promotes recovery from injury or ailment.

Figure 1A:
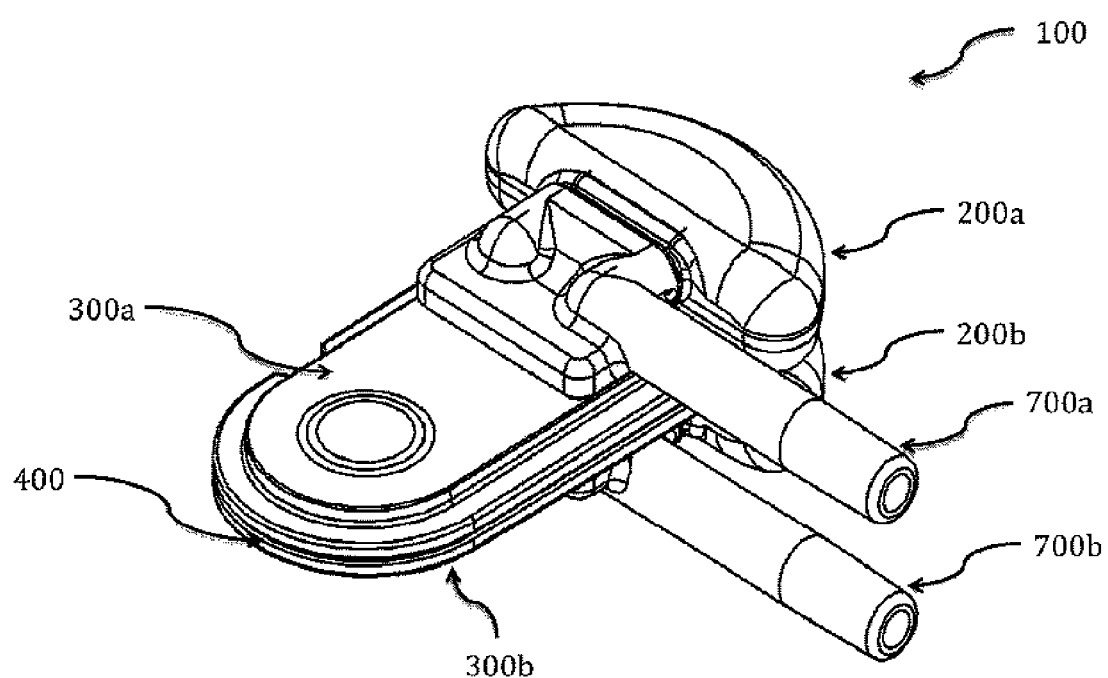
FIGS. 1A-1C illustrate a perspective view, rear elevation and top view, respectively, of a cartridge system in accordance with an embodiment of the present invention.
Figure 1B:
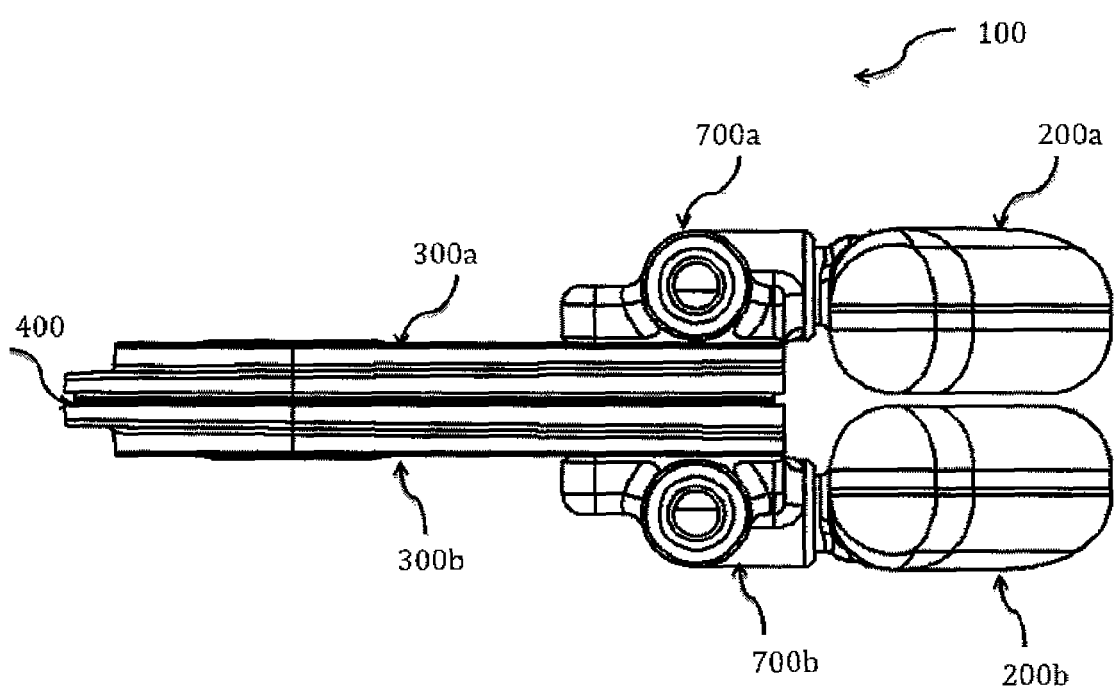
Figure 1C:
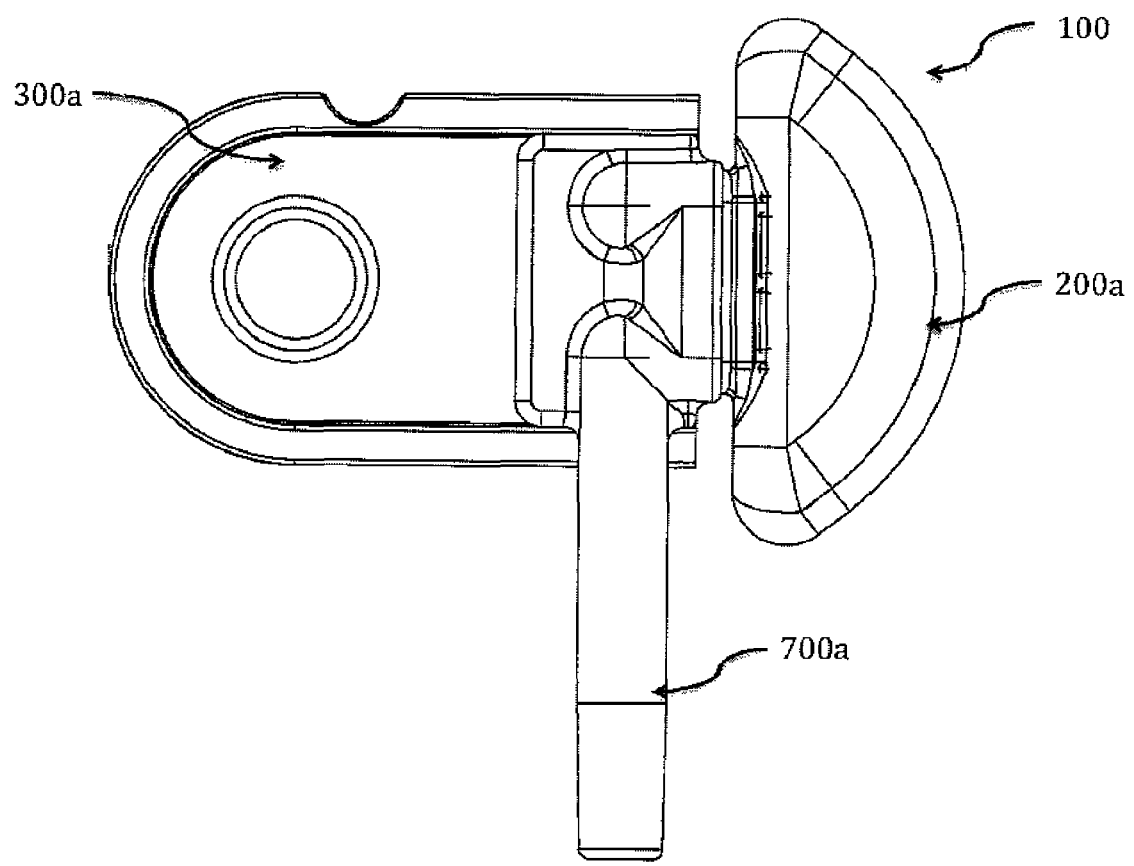

Referring now to the drawings, where like elements are designated by like reference numerals, FIGS. 1A-1C illustrate a cartridge system 100 in accordance with an embodiment of the invention. The cartridge system 100 includes a plurality of reservoirs 200a, 200b, a plurality of pump body inserts 300a, 300b, a pump membrane 400, and a plurality of inlet/outlet members 700a, 700b.

TABLE 1

Cartridge System of the Present Invention

Reservoir Shell

Figure 8A:
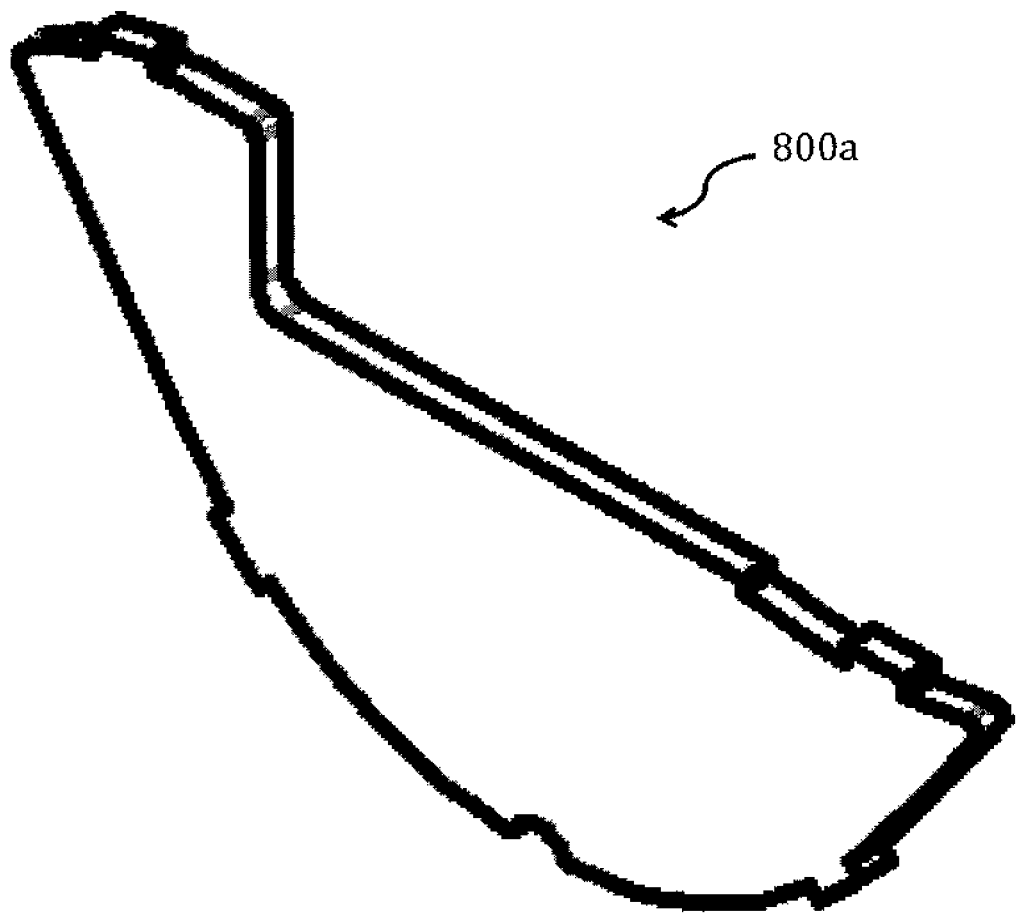
FIGS. 8A-8C illustrate a perspective view, respectively, of a first housing, a second housing, and a third housing that collectively comprise a reservoir shell of the cartridge system in accordance with an embodiment of the present invention.
Figure 8B:
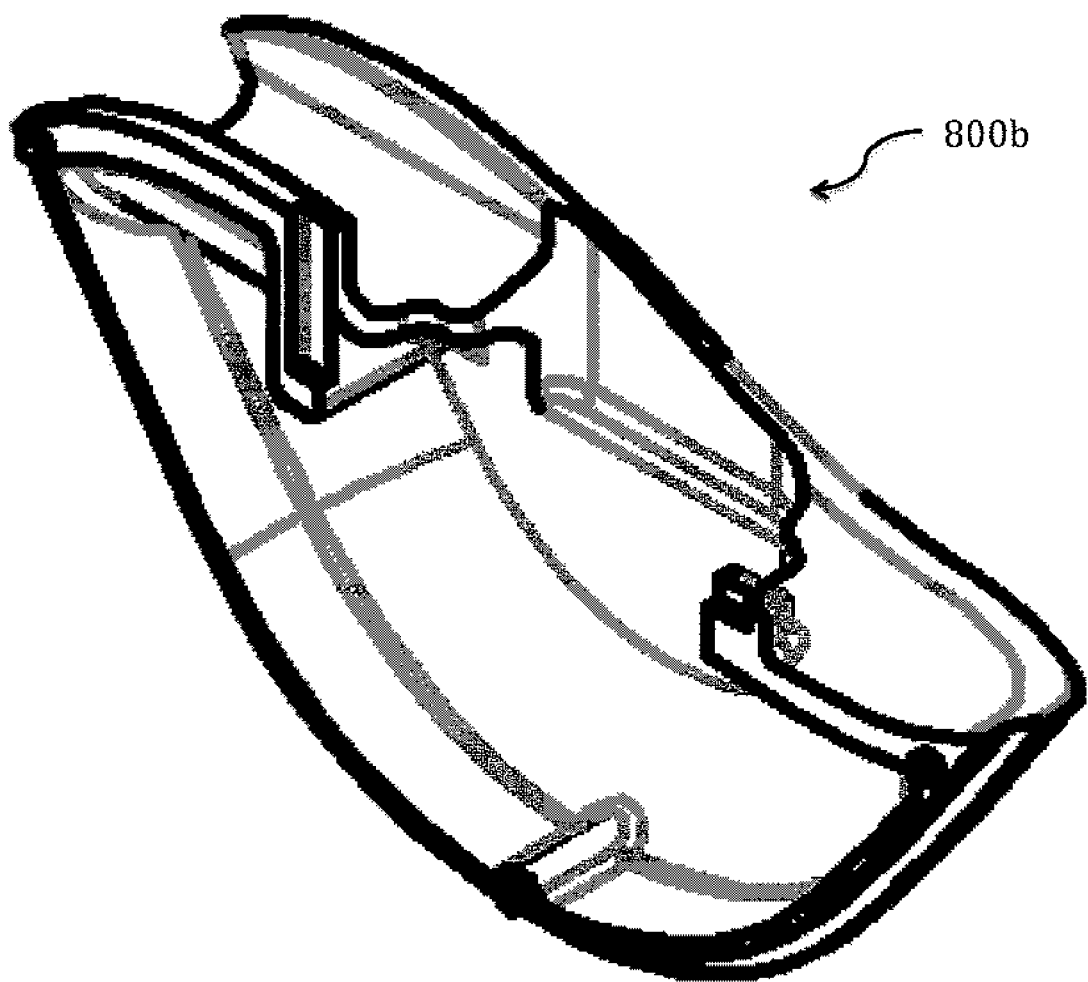
Figure 8C:
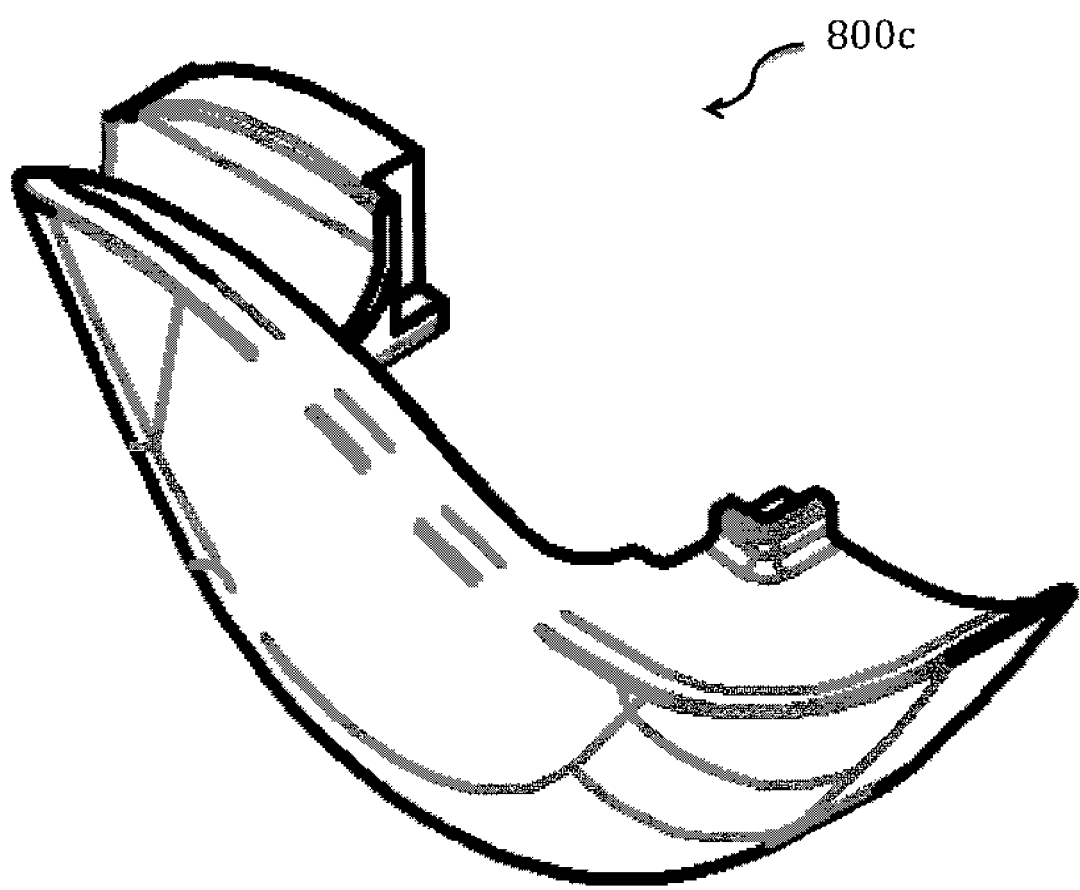

| | |
|---|---|
| Overall dimensions: | 1.56" (length) × 0.80" (width) × 0.71" (height) |
| Basic shape: | Shape as shown in FIGS. 8A-8C |
| Material: | RTP 699 × 122676 NS - Acrylonitrile Butadiene Styrene (ABS) Medical Grade |
| Number: | Preferably, two |

Reservoir

Figure 2A:
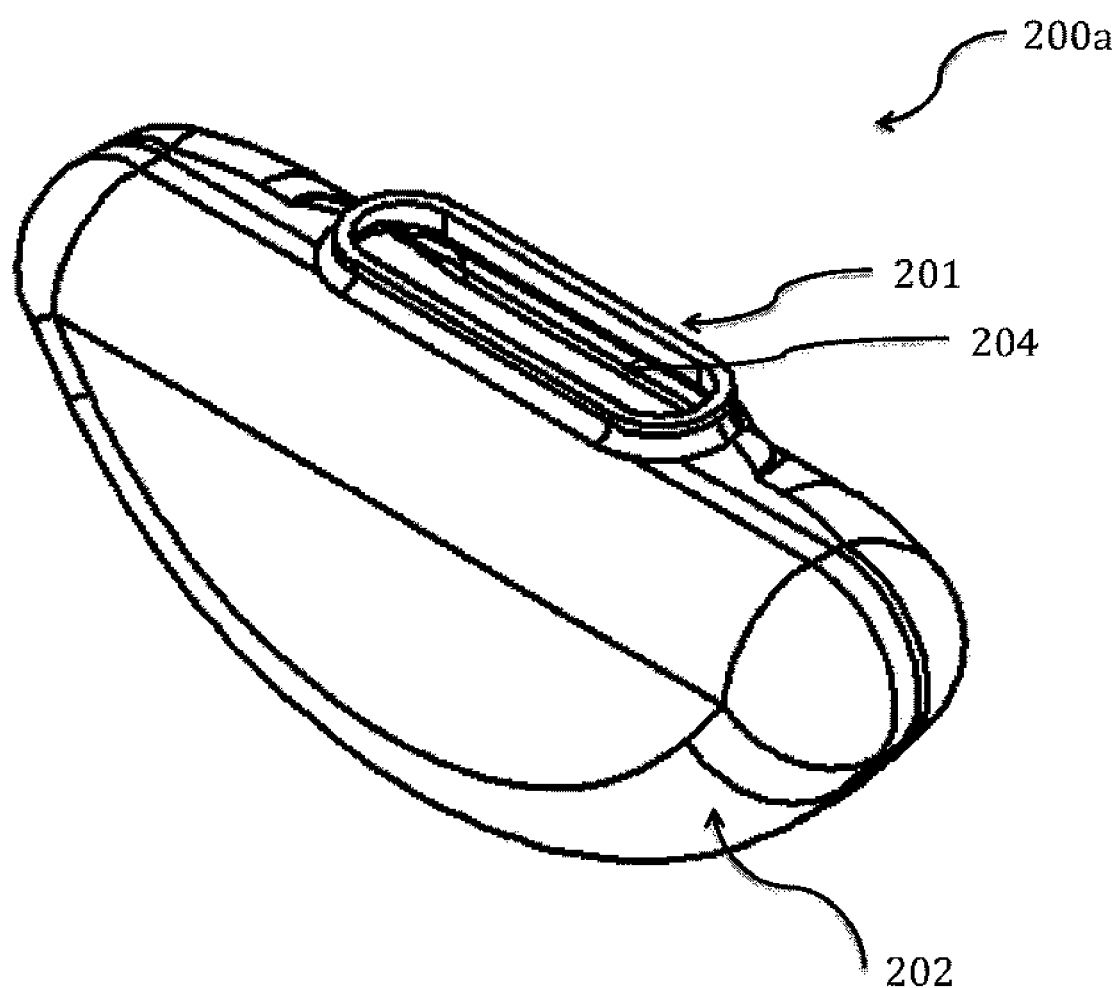
FIGS. 2A-2C illustrate a perspective view, front view and top view, respectively, of a reservoir of the cartridge system in accordance with an embodiment of the present invention.
Figure 2B:
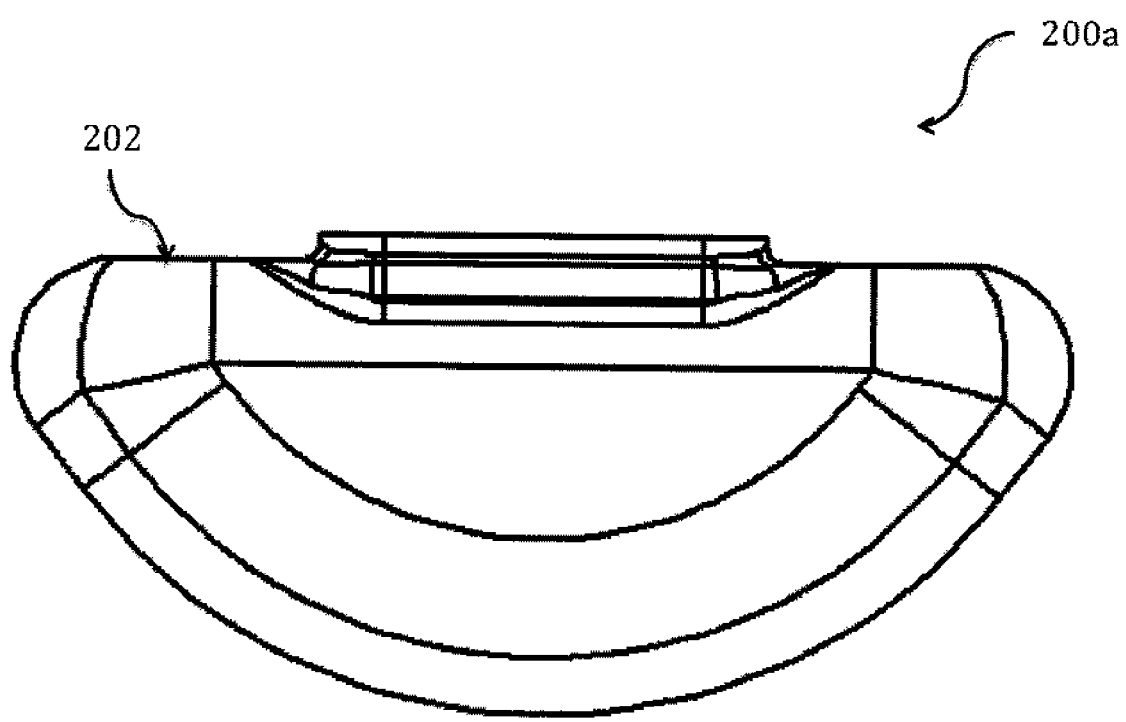
Figure 2C:
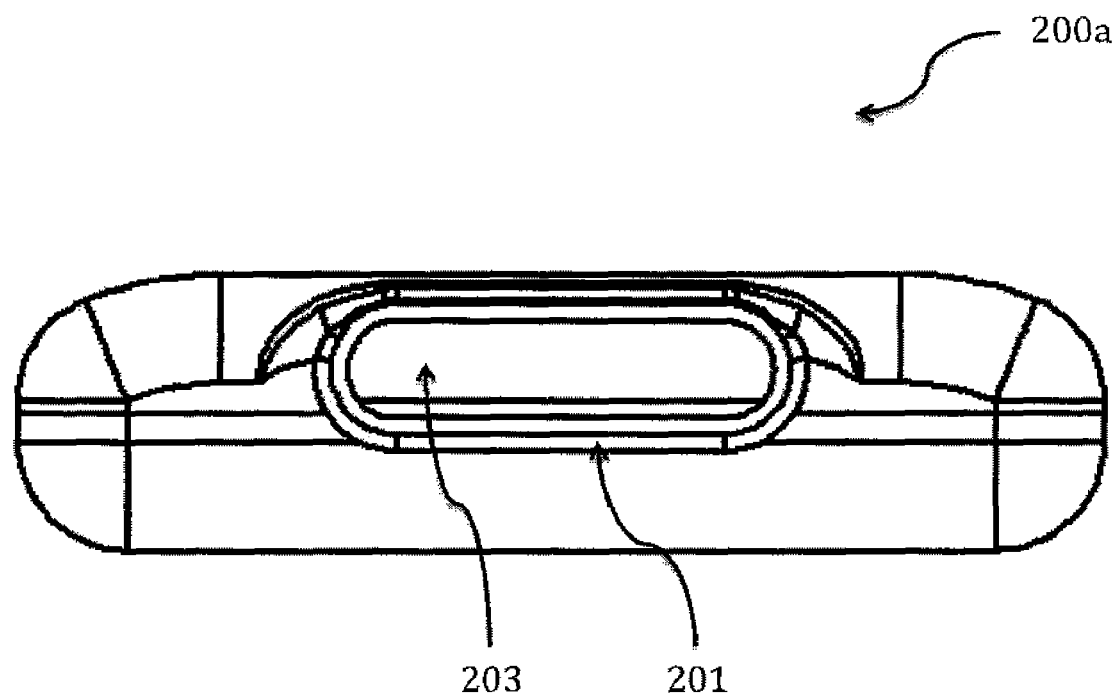

| | |
|---|---|
| Overall dimensions: | 0.99" (length) × 0.46" (width) × 0.26" (height) |
| Basic shape: | Shape as shown in FIGS. 2A-2C, and made of a material from a group consisting of elastomer, and the material having property such that the geometry is deformable |
| Material: | Silastic Q7-4840 or Medical Grade Polyisoprene |
| Number: | Preferably, two |

Pump Body Insert

| | |
|---|---|
| Overall dimensions: | 1.1" (length) × 0.7" (width) × 0.09" (height) |
| Basic shape: | Shape as shown in FIGS. 3A-3F, and having a plurality of flow channels, a fluid receiving opening, and a fluid discharge opening |
| Material: | Clear polypropylene homopolymer |
| Number: | Preferably, two |

Inlet/Outlet Member

| | |
|---|---|
| Overall dimensions: | 1.37" (length) × 0.49" (width) × 0.2" (height) |
| Basic shape: | Shape as shown in FIGS. 7A-7F, and having a receiving opening, a fluid discharge opening, and a fluid outlet component |
| Material: | Clear polypropylene homopolymer |
| Number: | Preferably, two |

Magnets

| | |
|---|---|
| Overall dimensions: | 0.13" (diameter) × 0.06" (height) |
| Basic shape: | Cylindrical |
| Material: | Neodymium-iron-boron grade N42 magnets, gold plated NdFeB |
| Number: | Preferably, two |

Pump Membrane

Figure 4A:
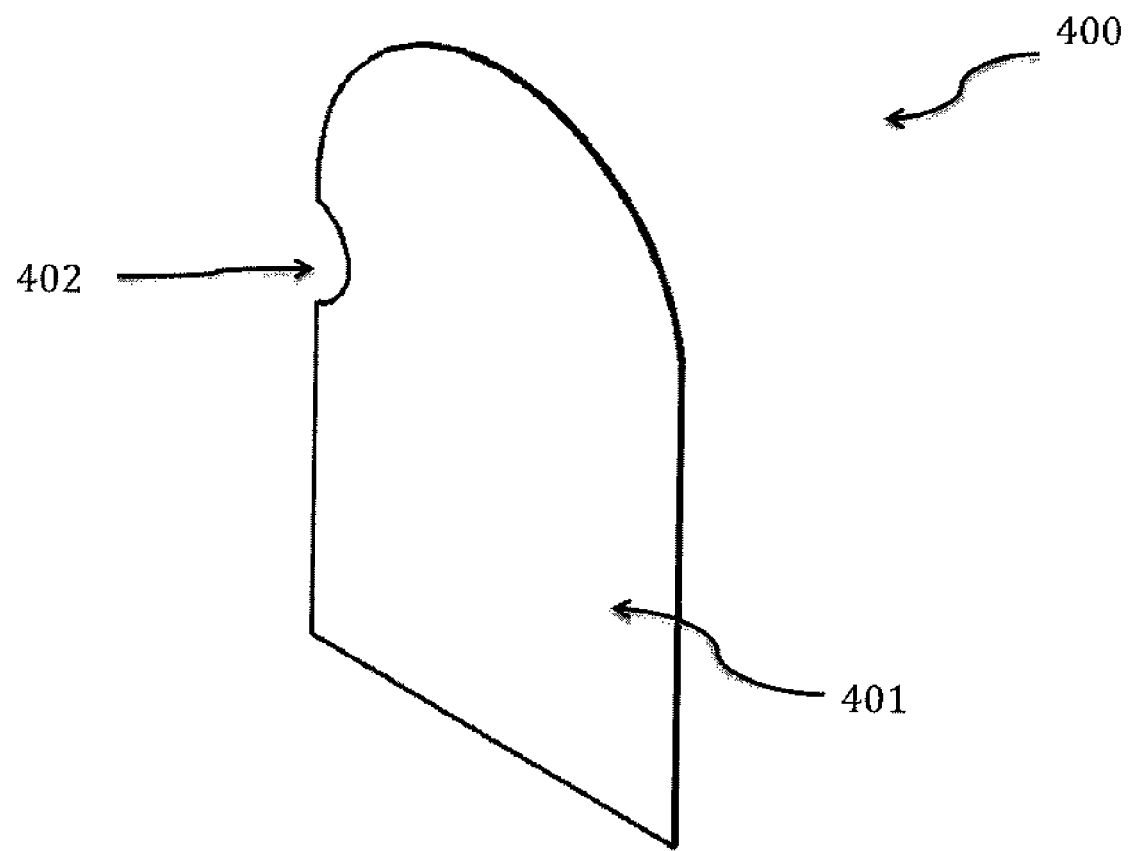
FIGS. 4A-4B illustrate a perspective view and front view, respectively, of a pump membrane of the cartridge system in accordance with an embodiment of the present invention.
Figure 4B:
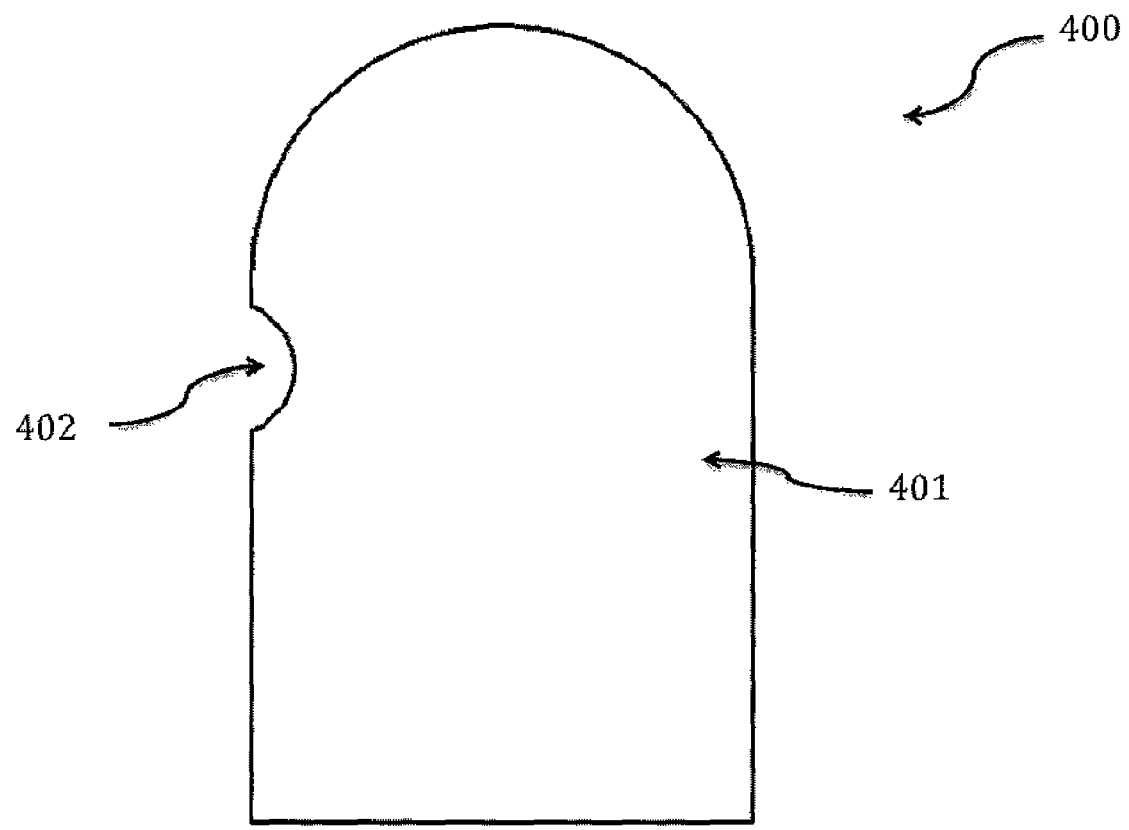

| | |
|---|---|
| Overall dimensions: | 1.07" (length) × 0.67" (width) × 0.01" (thickness) |
| Basic shape: | Shape as shown in FIGS. 4A-4B |
| Material: | Silastic Q7-4840 |
| Number: | One |

Valve Membrane

| | |
|---|---|
| Overall dimensions: | 0.19" (diameter) × 0.04" (height) |
| Basic shape: | Cylindrical |
| Material: | Silastic Q7-4840 |
| Number: | Four |

Referring to FIGS. 2A-2C, a reservoir 200a having an opening 203 is shown. The reservoir 200a is preferably made of elastomers and preferably made by liquid injection molding of Silastic Q7-4840 or transfer molding of Medical Grade Polyisoprene.

The advantages of using polymer materials to make the reservoirs 200a, 200b, pump body inserts 300a, 300b, inlet/outlet members 700a, 700b, and any housing portion is that they can be made in any size, designed in any way and manufactured with biocompatible materials. The polymer reservoirs allow better use of the interior volume available within the pump body, and the collapsible nature of the material allows for more innovative methods for withdrawing the liquid contents. The methods used in the manufacture of the polymer components as well as the arrangement and design of the cartridge system lends itself to being readily adaptable to commonly used sterilization techniques such as gamma irradiation, steam sterilization, or fluidic chemical sterilization.

Figure 7A:
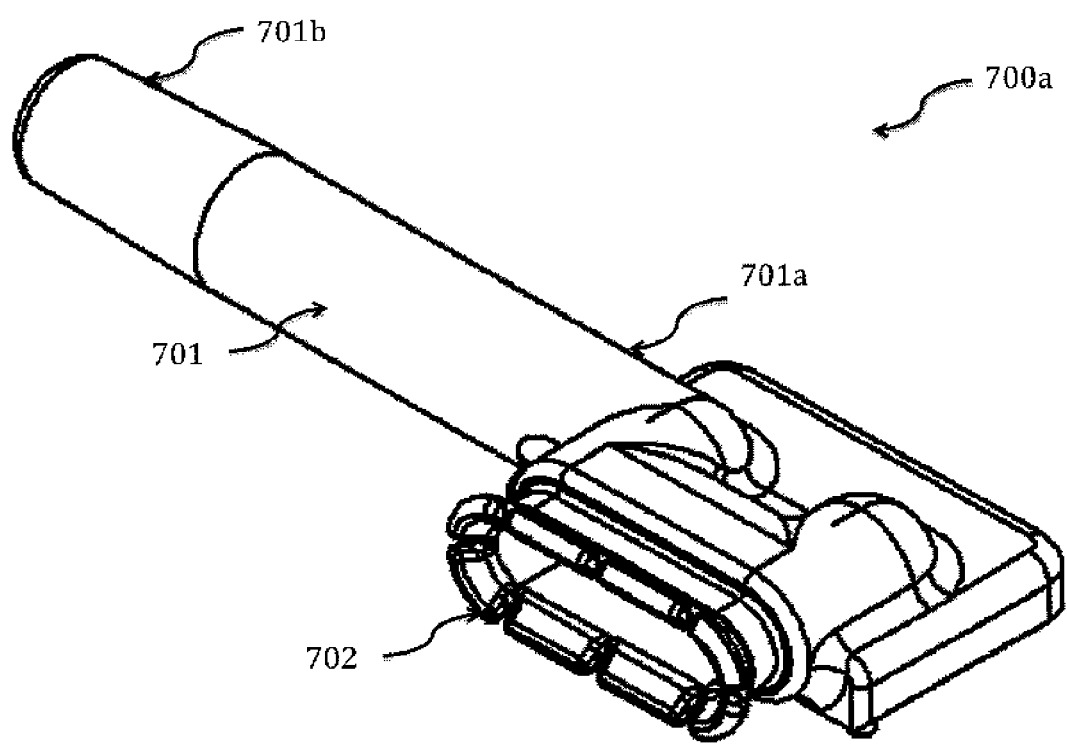
FIGS. 7A-7C illustrate a perspective view, bottom view and top view, respectively, of a first inlet/outlet member of the cartridge system in accordance with an embodiment of the present invention.

The reservoir 200a has a substantially symmetrical body having a top end (not shown), a bottom end (not shown), an inner wall 204, and an outer wall 202. The top end of the reservoir 200a has an opening 203 that is encircled by the inner wall 204 and the outer wall 202. At the top end, the inner wall 204 and the outer wall 202 project in an upward direction to form a female part 201. The female part 201 is preferably of length about 0.42 inches. The female part 201 is securely engaged to a male part 702 (FIG. 7A) of an inlet/outlet member 700a (FIG. 7A).

The thickness of the reservoir 200a is preferably between 50μ and 200μ. The top end, the bottom end, the inner wall 204 and the outer wall 202 enclose a reservoir space for storage of fluid medicament. The reservoirs 200a, 200b of the cartridge system 100 are preferably dual reservoir, pre-filled with fluid medicaments, each of the reservoirs 200a, 200b capable of holding 1.5 ml of fluid medicament. Although FIGS. 2A-2C illustrate reservoir 200a, it must be understood that reservoir 200b is substantially the same.

In another preferred embodiment of the invention, the reservoirs 200a, 200b can be any free-form shaped body. The reservoirs 200a, 200b can be mounted within a reservoir shell 206, the inside of the reservoir shell 206 having an insulation layer 205.

Figure 2D:
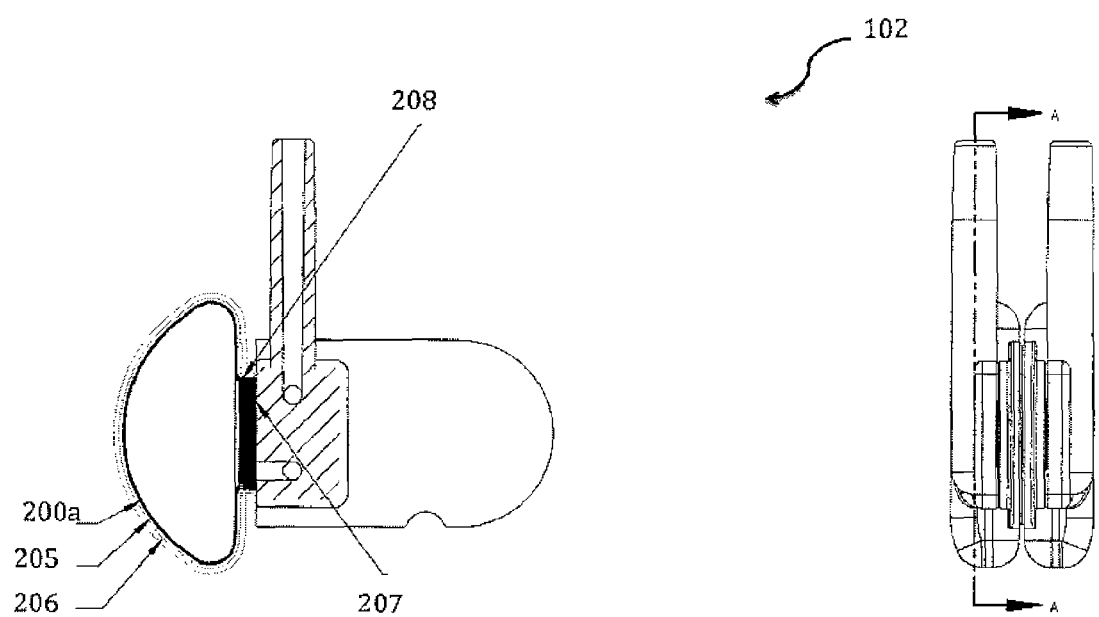
FIG. 2D illustrates a sectional view of a reservoir of the cartridge system in accordance with another embodiment of the present invention.

In yet another preferred embodiment of the invention, as shown in FIG. 2D, the cartridge assembly 100 includes the reservoir 200a mounted within a reservoir shell 206. The inside of the reservoir shell 206 is provided with an insulation layer 205 that enables temperature control of the fluid medicament within the reservoir 200a. A cap 207 can be coupled, for example, through molding 208, to the inner wall 204 near the opening 203. The reservoir shell 206 is coupled to the cap 207 and the cap 207 is securely engaged to a male part of the inlet/outlet members 700a, 700b (FIGS. 7A-7F).

Figure 2E:
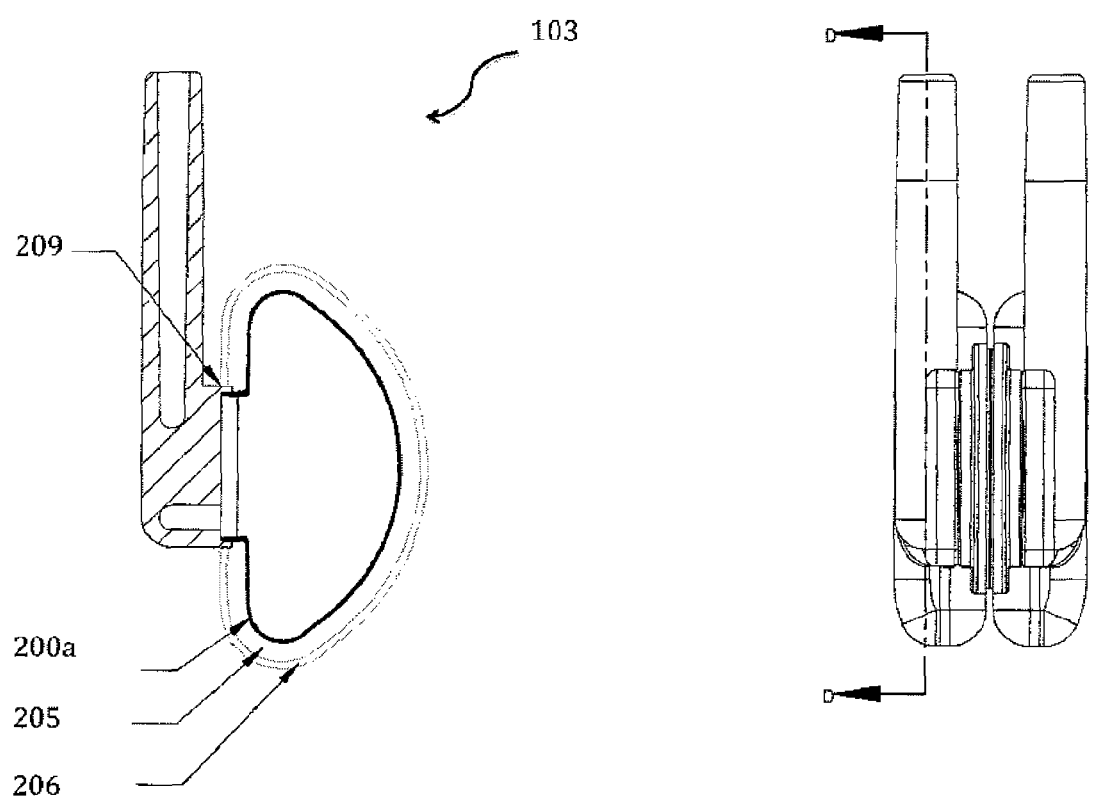
FIG. 2E illustrates a sectional view of a reservoir of the cartridge system in accordance with yet another embodiment of the present invention.

In yet another preferred embodiment of the invention, as shown in FIG. 2E, the cartridge assembly 100 includes the reservoir 200a mounted within a reservoir shell 206. The inside of the reservoir shell 206 is provided with an insulation layer 205 that enables temperature control of the fluid medicament within the reservoir 200a. A cap 207 can be coupled to the inner wall 204 near the opening 203. The reservoir shell 206 is coupled to the cap 207 and the cap 207 is threadedly 209 engaged to a male part of the inlet/outlet members 700a, 700b (FIG. 7A-7F).

It is to be understood that the reservoirs 200a, 200b mounted within a reservoir shell 206 having an insulation layer 205 or without the reservoir shell 206 can include a cap for removably closing the opening 203. The reservoirs may be designed to work with any drug delivery device for delivery of medicaments.

Figure 3A:
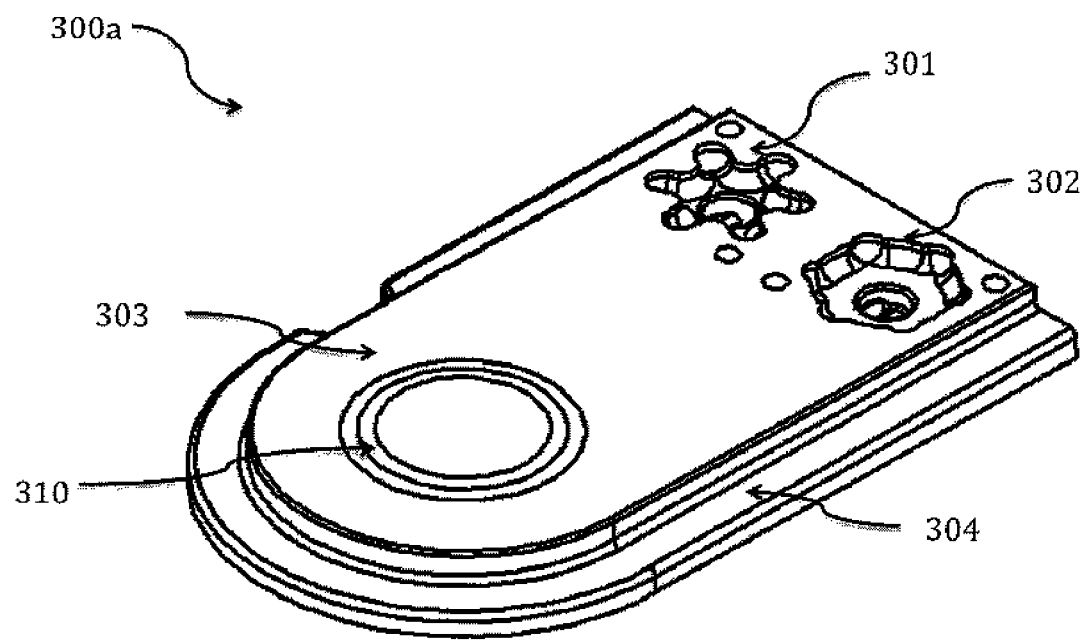
FIGS. 3A-3C illustrate a perspective view, bottom view and top view, respectively, of a first pump body insert of the cartridge system in accordance with an embodiment of the present invention.
Figure 3B:
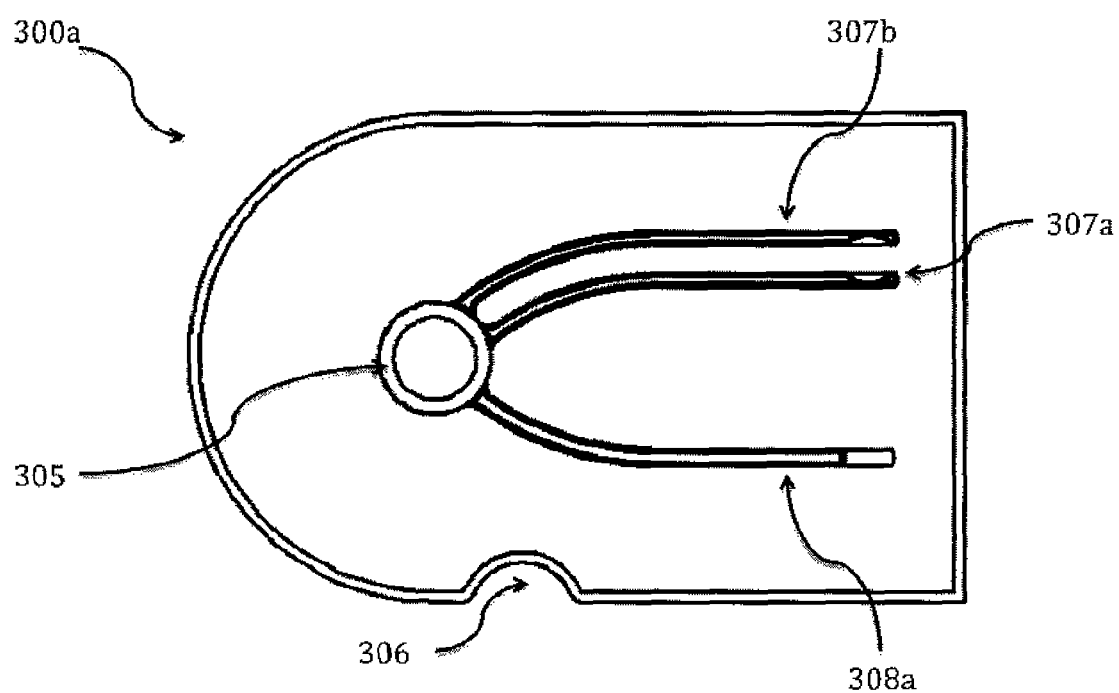
Figure 3C:
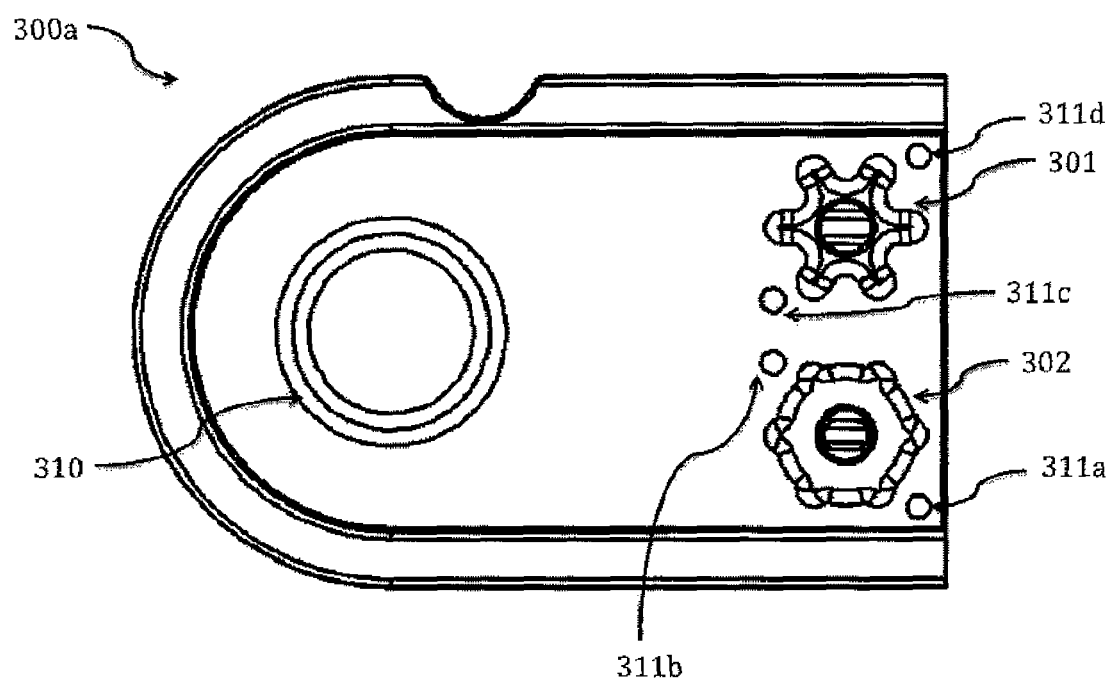
Figure 5:
FIG. 5 illustrates perspective, front and top views of a magnet of the cartridge system in accordance with an embodiment of the present invention.
Figure 5:
Figure 5:
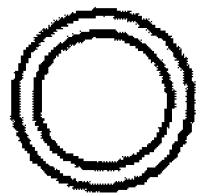

Referring to FIGS. 3A-3C, a first pump body insert 300a having a fluid receiving opening 301, and a fluid discharge opening 302 is shown. The first pump body insert 300a also includes a plurality of output channels 307a, 307b, for example, two output channels, and a plurality of input channels 308a, for example, one input channel. The plurality of output channels 307a, 307b and the plurality of input channels 308a are in fluid communication with the fluid discharge opening 302, and the fluid receiving opening 301, respectively. The plurality of output channels 307a, 307b and input channels 308a are designed to provide membrane support thereby preventing deformation and reverse flow of fluids. The first pump body insert 300a has an opening 305 to house a magnet 500 (FIG. 5). Apertures 311a, 311b, 311c, 311d can be used to align and/or secure the first pump body insert 300a to other elements of the cartridge system 100.

Figure 3D:
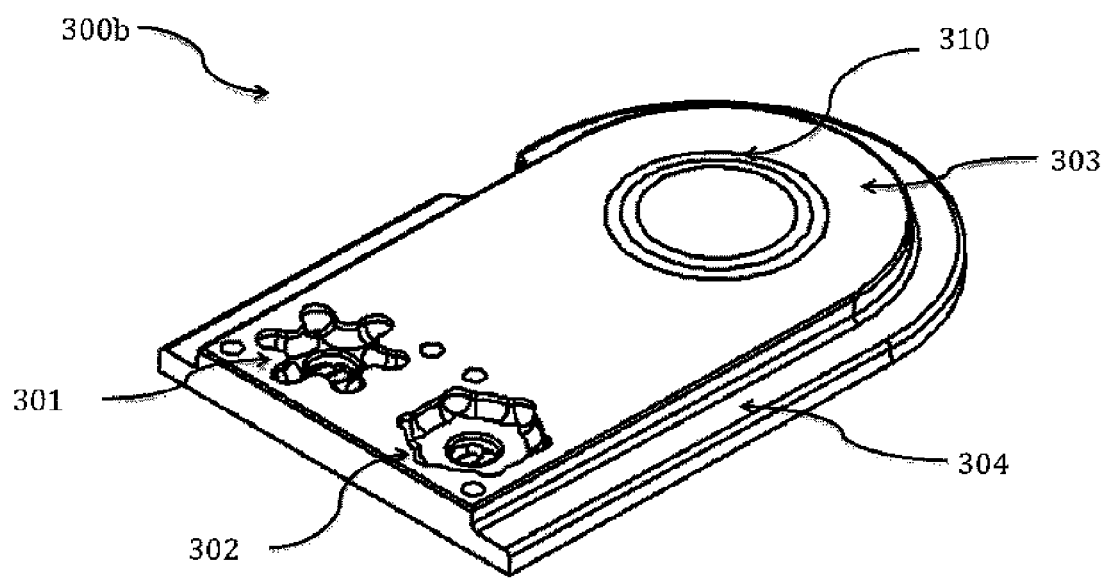
FIGS. 3D-3F illustrate a perspective view, bottom view and top view, respectively, of a second pump body insert of the cartridge system in accordance with an embodiment of the present invention.
Figure 3E:
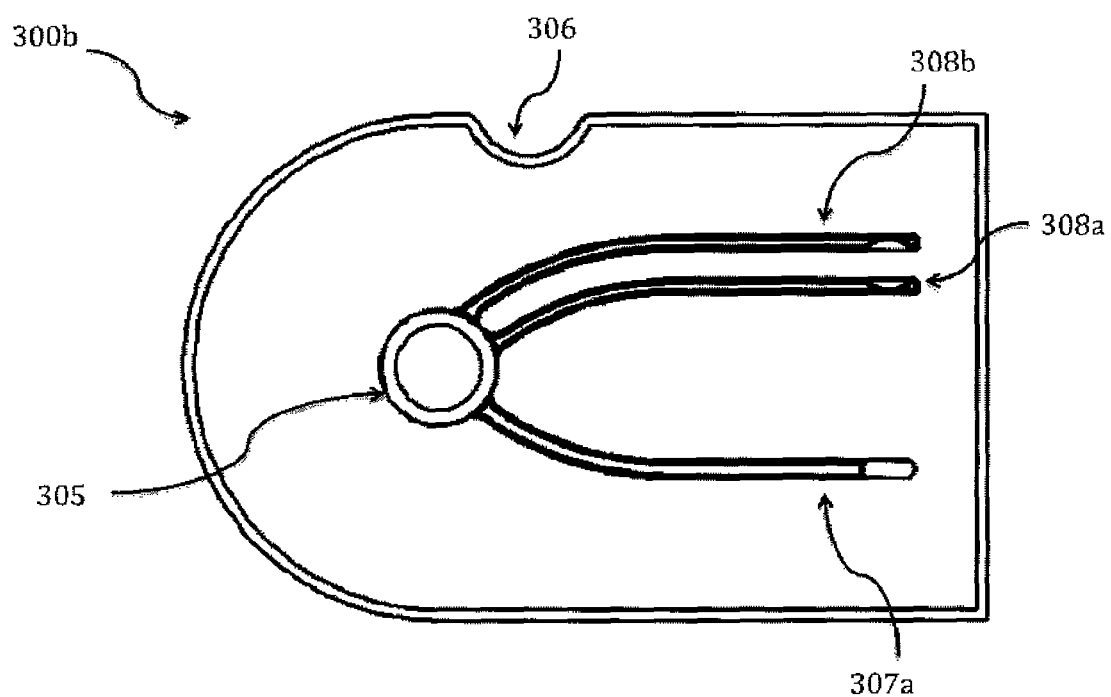
Figure 3F:
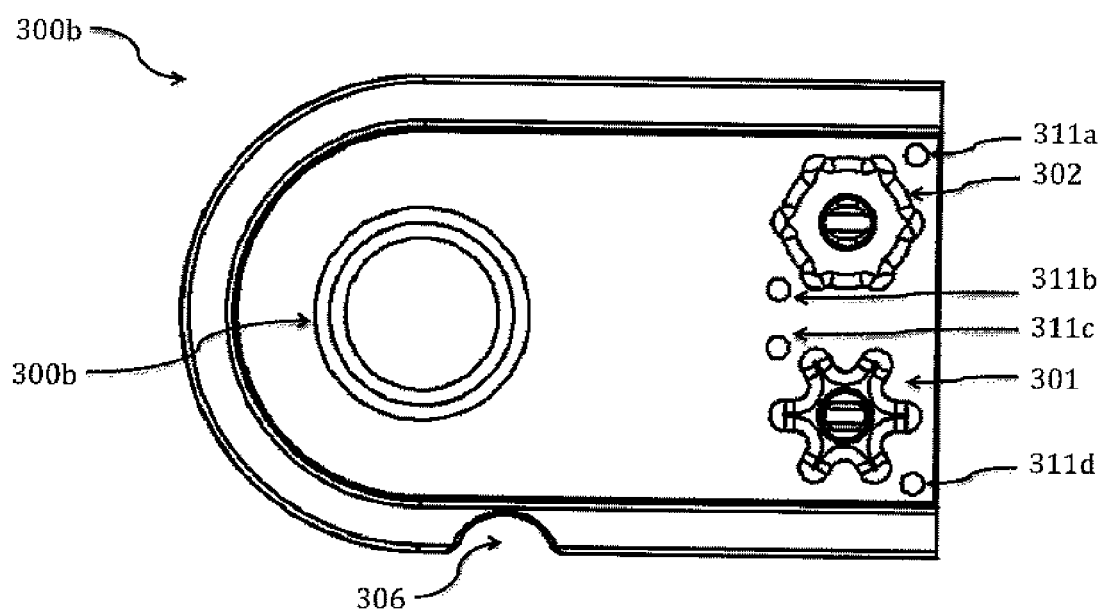

The second pump body insert 300b, shown in FIGS. 3D-3F, is substantially symmetrical in geometry to the first pump body insert 300a except having a plurality of output channels 307a, for example, one output channel, and a plurality of input channels 308a, 308b, for example, two input channels. The first pump body insert 300a and second pump body insert 300b are preferably made of clear polypropylene homopolymer.

The cartridge system 100 has a pump membrane 400 as shown in FIGS. 4A-4B. The pump membrane 400 is a biocompatible elastomer membrane, preferably made of Silastic Q7-4840. The pump membrane 400 is placed between two disk magnets 500, shown in FIG. 5, which are housed within opening 305 of the first pump body insert 300a and the second pump body insert 300b. The disk magnets 500 are preferably gold-plated neodymium-iron-boron grade N42 magnets. The volume of flow of fluid medicaments in the cartridge system 100 is related to the diameter of the magnets 500 and the stroke length. The stroke length can be electromagnetically controlled and monitored by a driver feedback system.

Figure 7B:
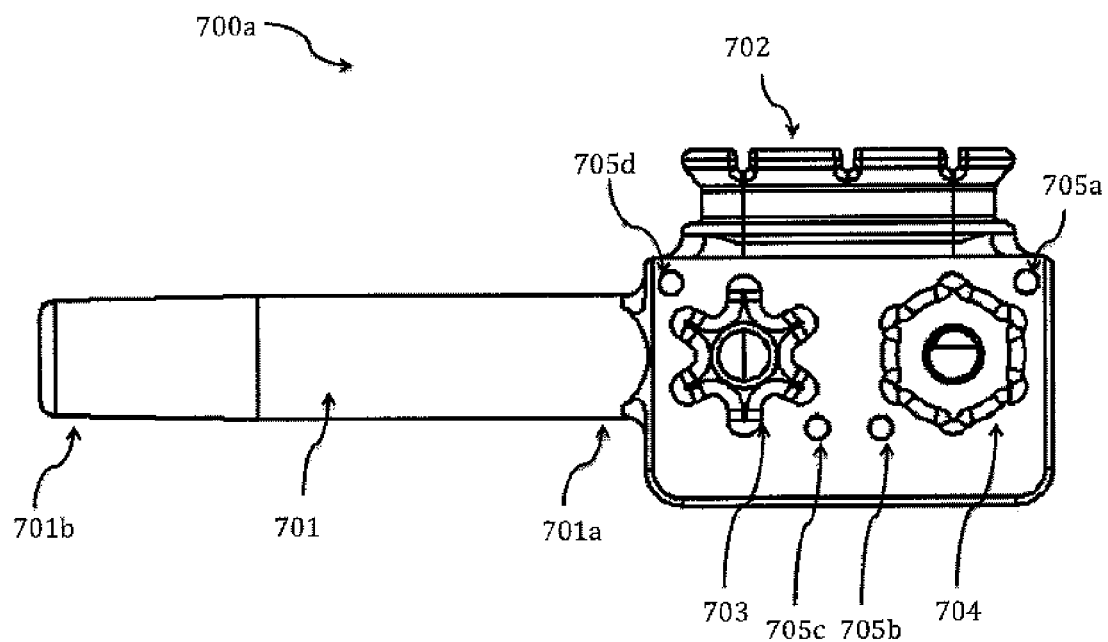
Figure 7C:
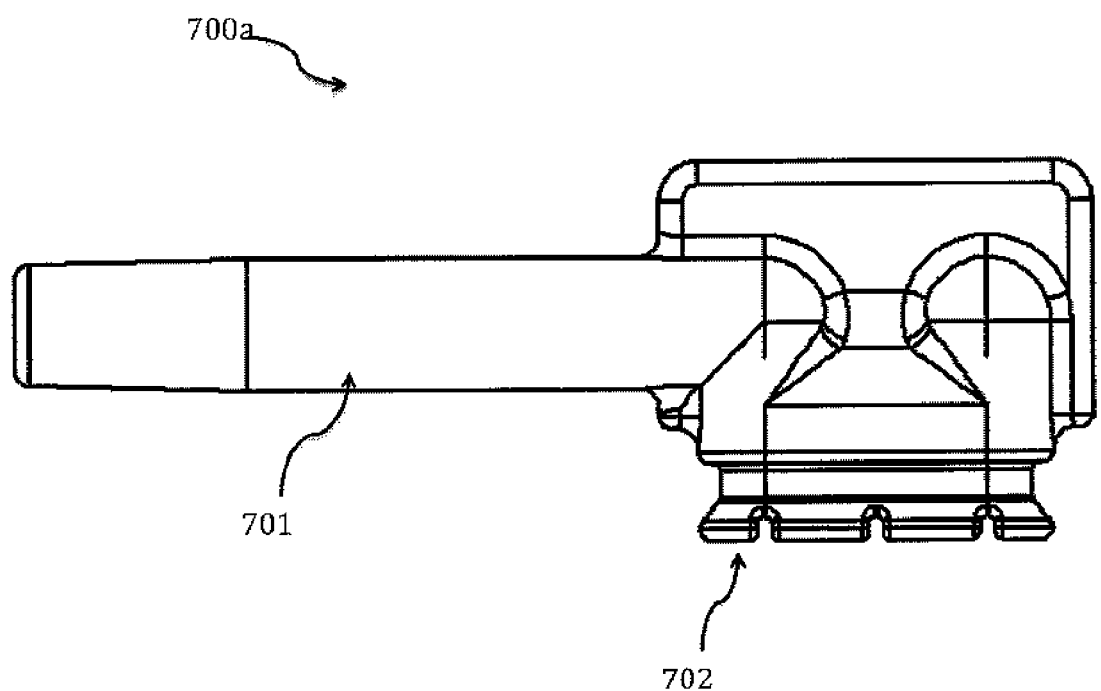

Referring to FIGS. 7A-7C, a first inlet/outlet member 700a having a fluid receiving opening 704, and a fluid discharge opening 703 is shown. The inlet/outlet member 700a has a fluid outlet component 701 having a proximal end 701b, a distal end 701a and a cylindrical body connecting the distal and the proximal ends to form a hollow for receiving fluid medicament. In one embodiment, the proximal end 701b can preferably have a tapered end with a luer slip. The inlet/outlet member 700a includes a male part 702 that securely engages to the female part 201 of the reservoir 200a. Apertures 705a, 705b, 705c, 705d can be used to align and/or secure the first inlet/outlet member 700a to other elements of the cartridge system 100.

Figure 7D:
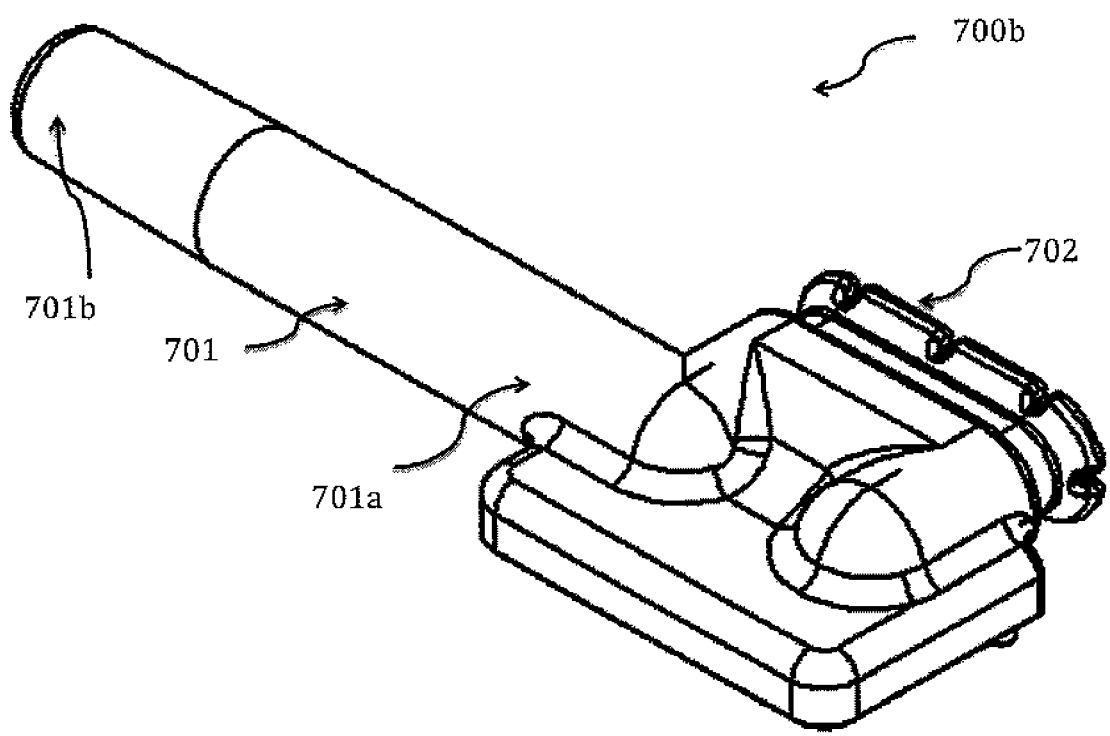
FIGS. 7D-7F illustrate a perspective view, bottom view and top view, respectively, of a second inlet/outlet member of the cartridge system in accordance with an embodiment of the present invention.
Figure 7E:
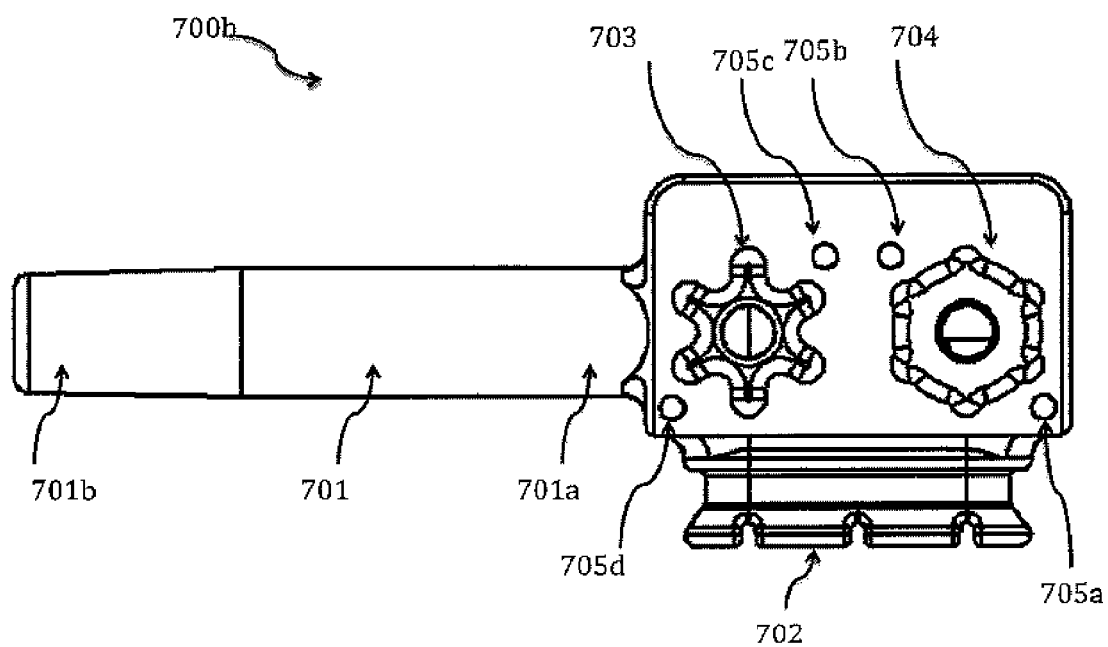
Figure 7F:
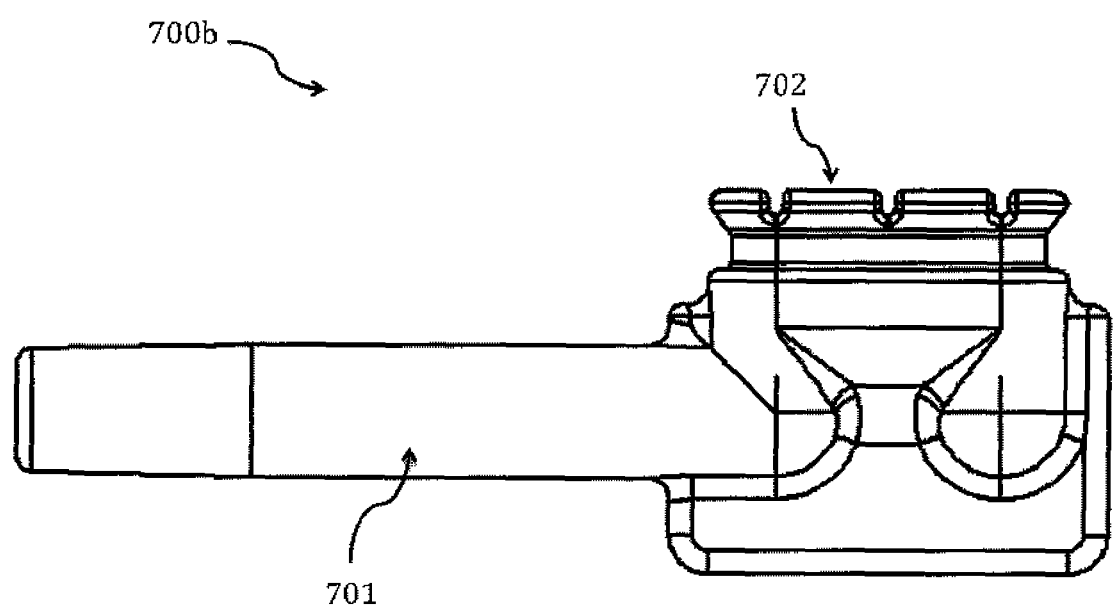

The second inlet/outlet member 700b, shown in FIGS. 7D-7F is substantially symmetrical in geometry to the first pump body insert 700a. Inlet/outlet members 700a, 700b are preferably made of clear polypropylene homopolymer.

The male part 702 of the inlet/outlet members 700a, 700b can have tooth-like channels to ensure that a low resistance path for fluid flow exists for all configurations of the reservoirs 200a, 200b. The reservoirs 200a, 200b, the pump body inserts 300a, 300b, the pump membrane 400, and the inlet/outlet members 700a, 700b are securely engaged using housing units 800a, 800b, 800c shown in FIGS. 8A-8C.

Figure 6:
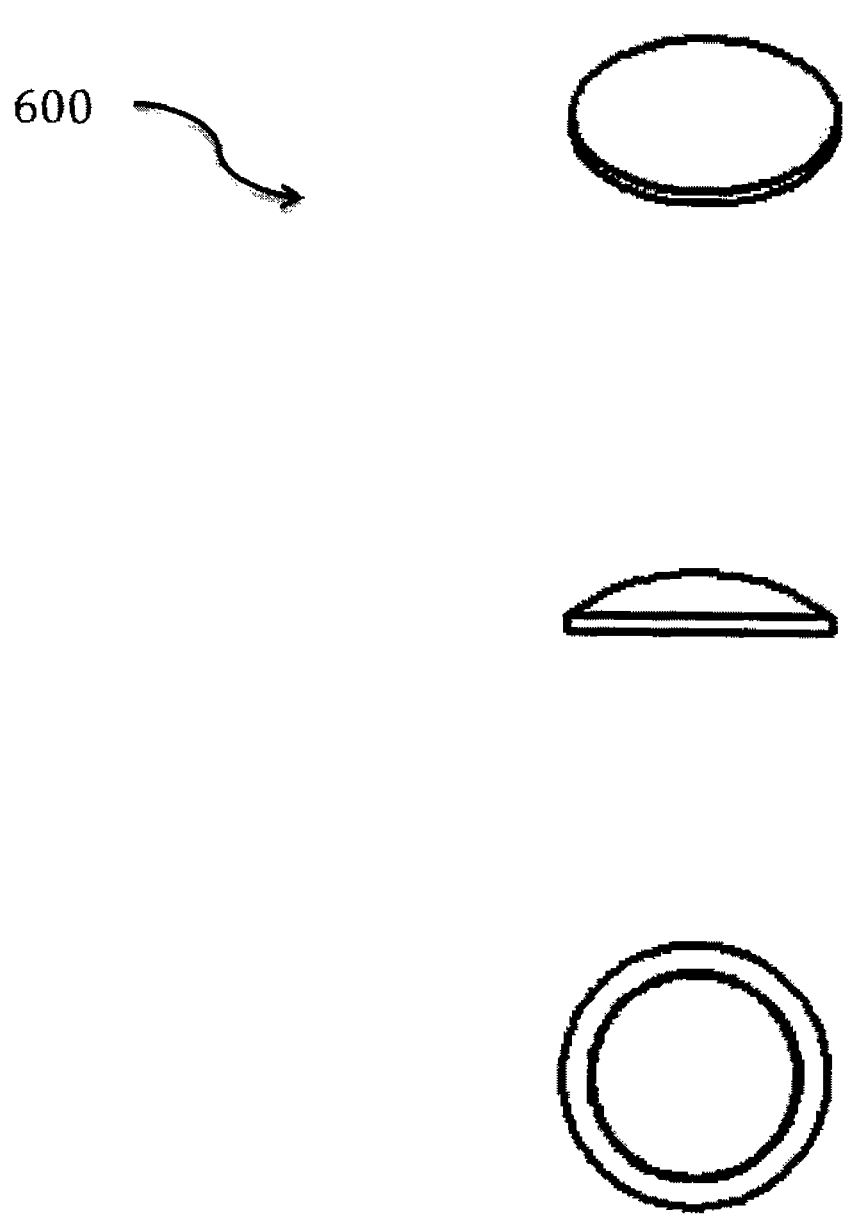
FIG. 6 illustrates perspective, front and top views of a valve membrane of the cartridge system in accordance with an embodiment of the present invention.

Four valve membranes 600, shown in FIG. 6, preferably made of Silastic Q7-4840, are placed between (i) the fluid receiving opening 301 of the pump body inserts 300a, 300b and the fluid receiving opening 704 of the inlet/out members 700a, 700b, and (ii) the fluid discharge opening 302 of the pump body inserts 300a, 300b and the fluid discharge opening 703 of the inlet/out members 700a, 700b. The introduction of the valve membranes 600 within said openings produce passive, one-way valves which direct fluid flow within the cartridge system 100.

When cartridge system 100 is assembled together, the first reservoir 200a, the fluid receiving opening 704 of the first inlet/outlet member 700a, the fluid receiving opening 301 of the first pump body insert 300a, the plurality of inlet channels 308a and the plurality of outlet channels 307a, 307b of the first pump body insert 300a, the fluid discharge opening 302 of the first pump body insert 300a, and the fluid discharge opening 703 and the fluid outlet component 701 of the first inlet/outlet member 700a are in fluid connection. Likewise, the second reservoir 200b, the fluid receiving opening 704 of the second inlet/outlet member 700b, the fluid receiving opening 301 of the second pump body insert 300b, the plurality of inlet channels 308a, 308b and the plurality of outlet channels 307a of the second pump body insert 300b, the fluid discharge opening 302 of the second pump body insert 300b, and the fluid discharge opening 703 and the fluid outlet component 701 of the second inlet/outlet member 700b are in fluid connection.

Figure 9A:
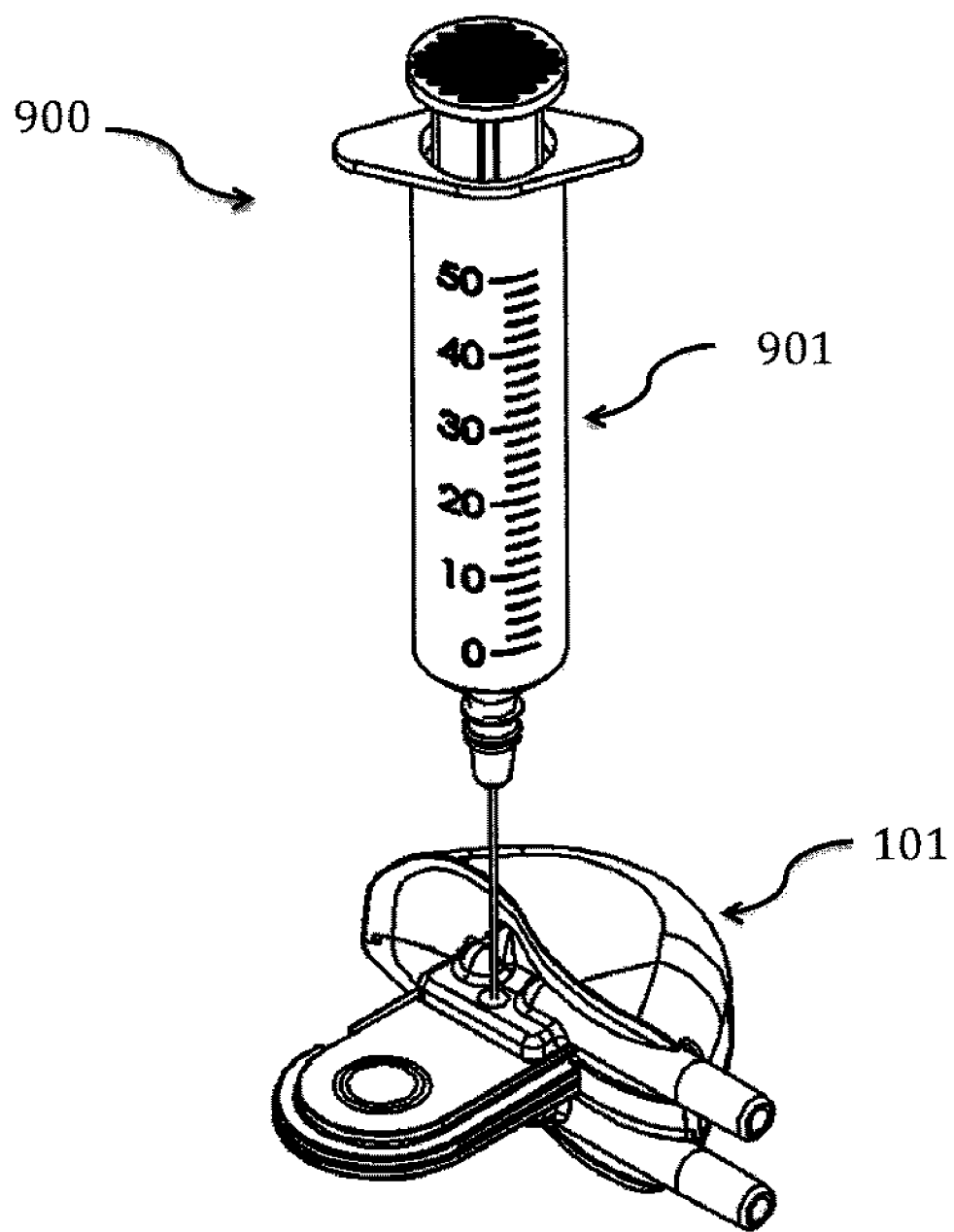
FIG. 9A illustrates a perspective view of a cartridge system, and a syringe, in accordance with another embodiment of the present invention.
Figure 9B:
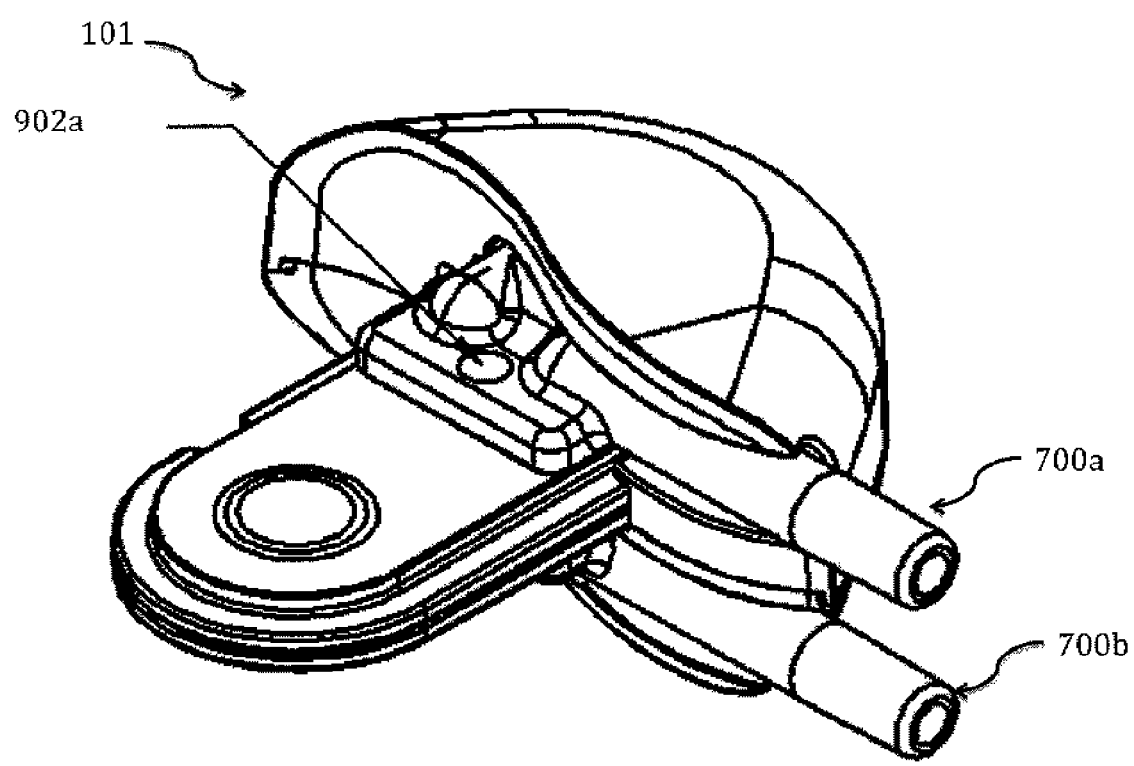
FIGS. 9B-9C illustrate perspective views of the cartridge system in accordance with another embodiment of the present invention.
Figure 9C:
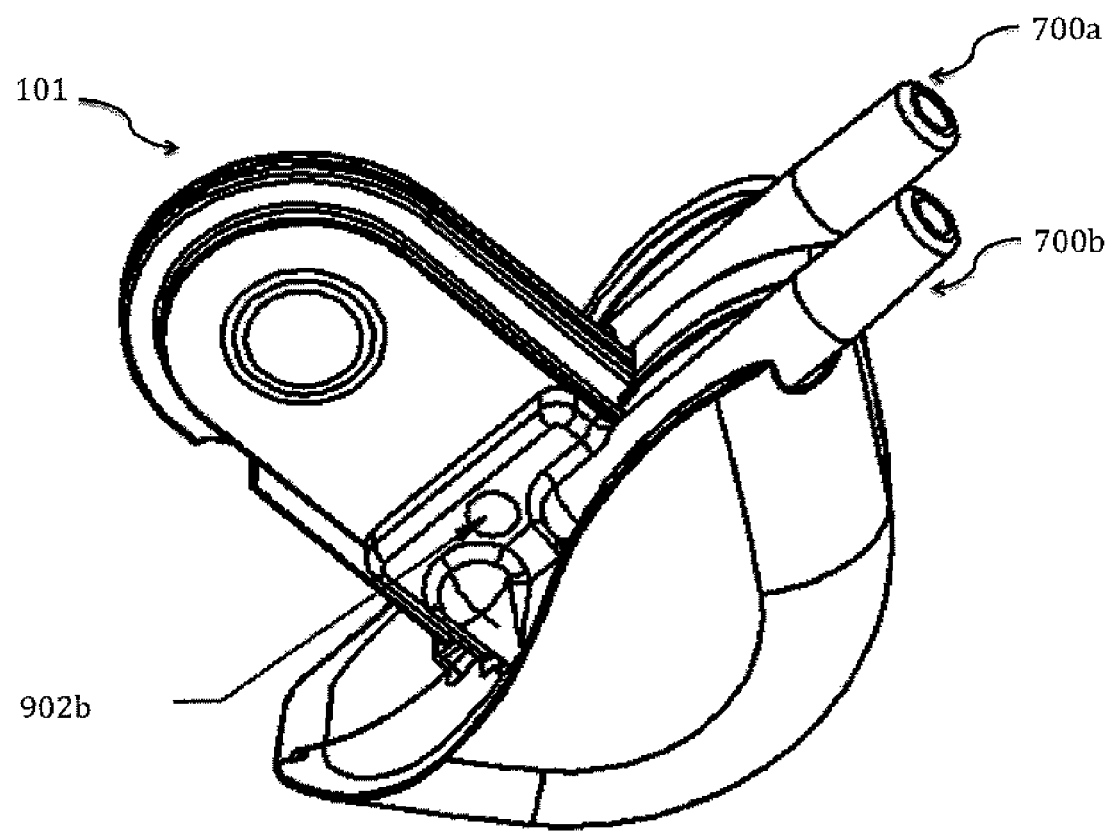
Figure 10A:
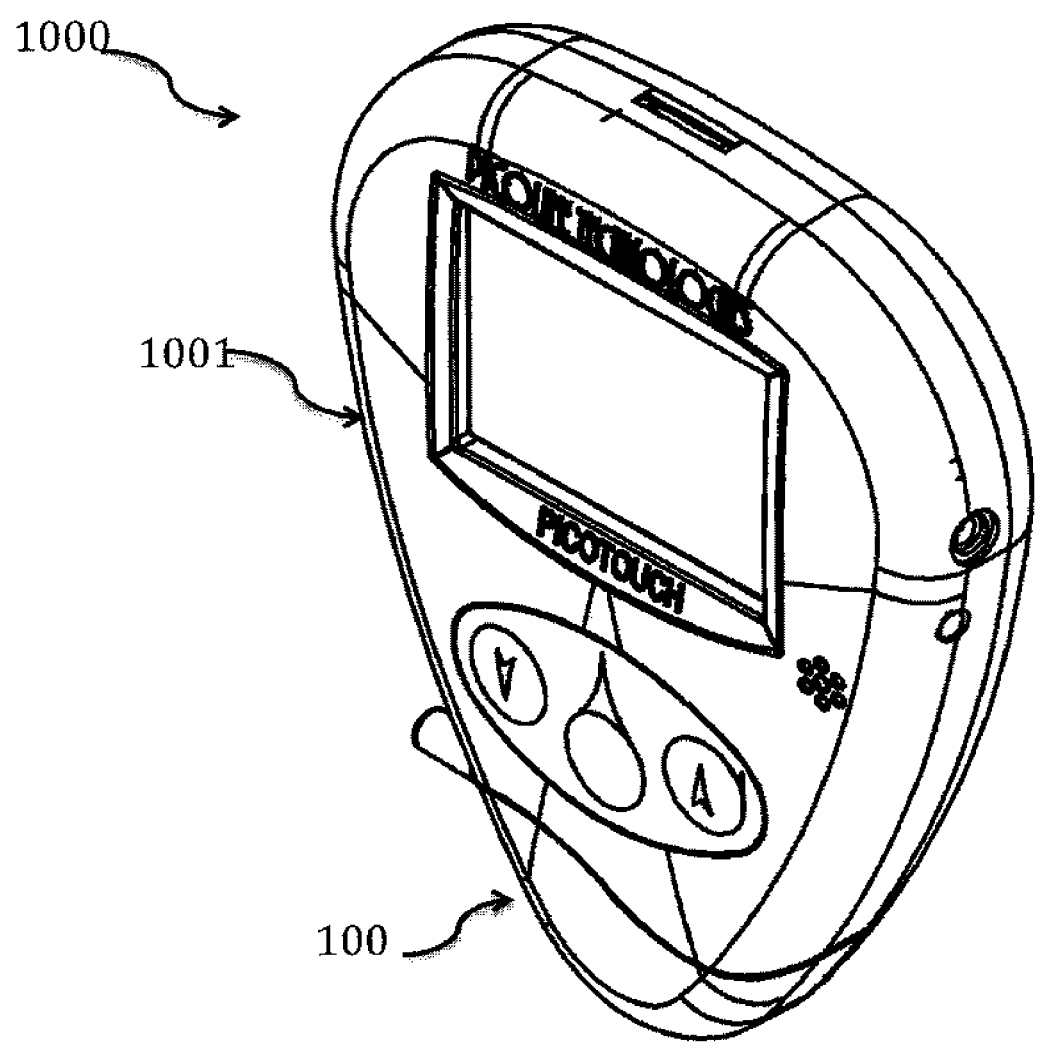
FIGS. 10A-10F illustrate a perspective view, front view, rear view, right side view, left side view, and bottom view, respectively, of a drug delivery device comprising a pump driver system and the cartridge system in accordance with an embodiment of the present invention.
Figure 10B:
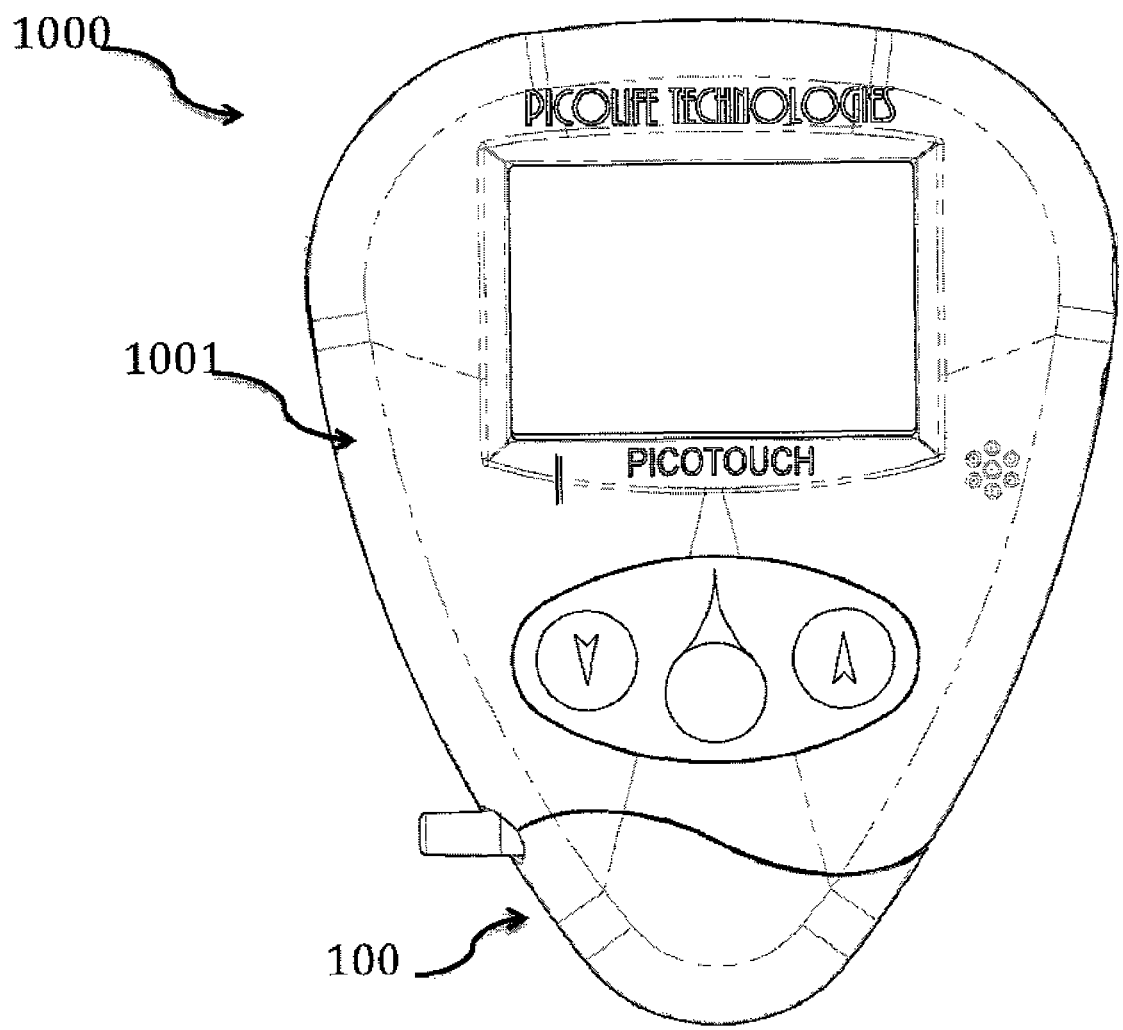
Figure 10C:
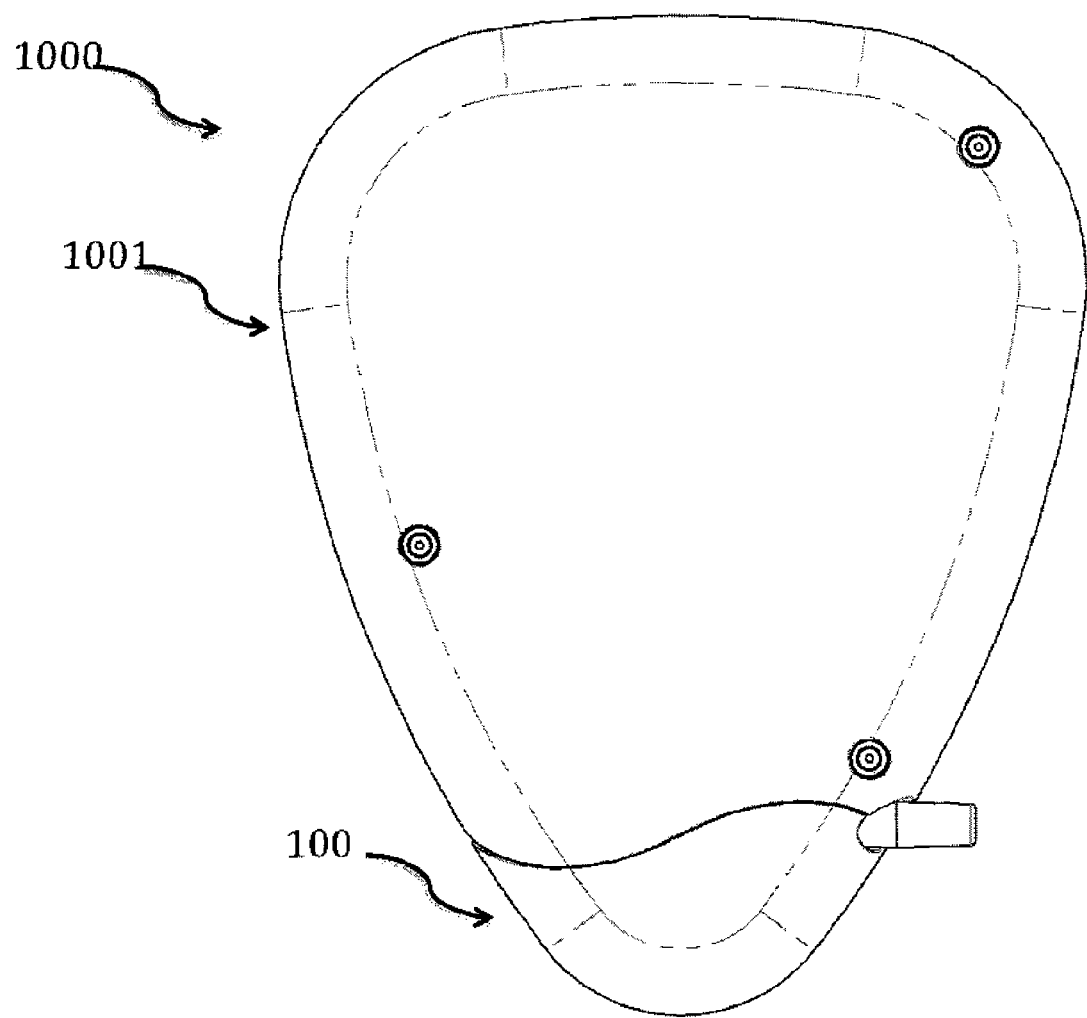
Figure 10D:
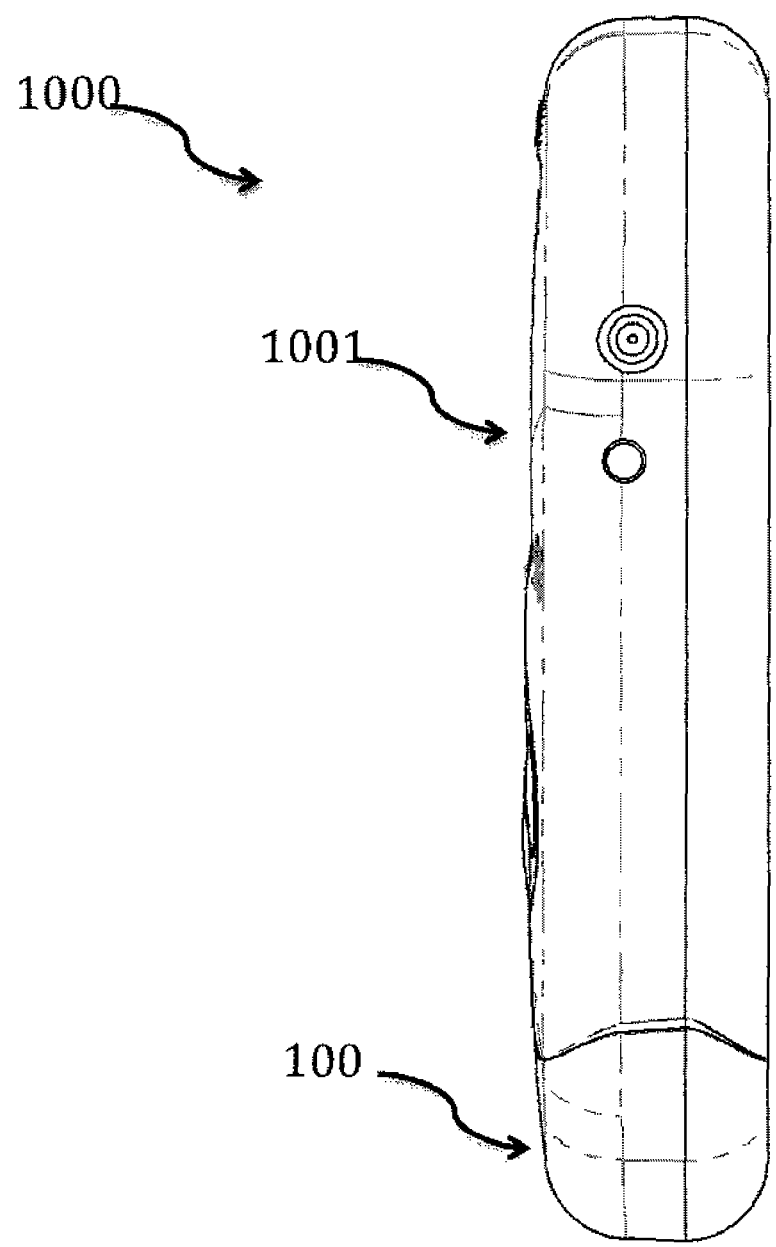
Figure 10E:
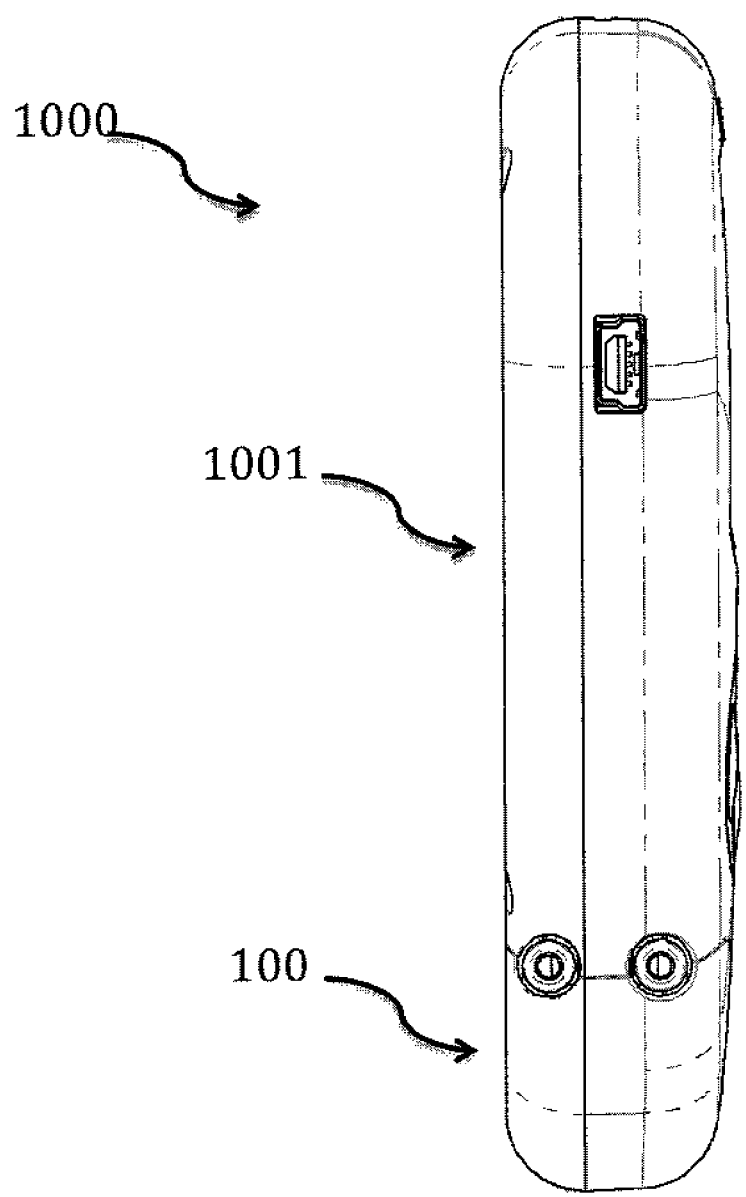
Figure 10F:
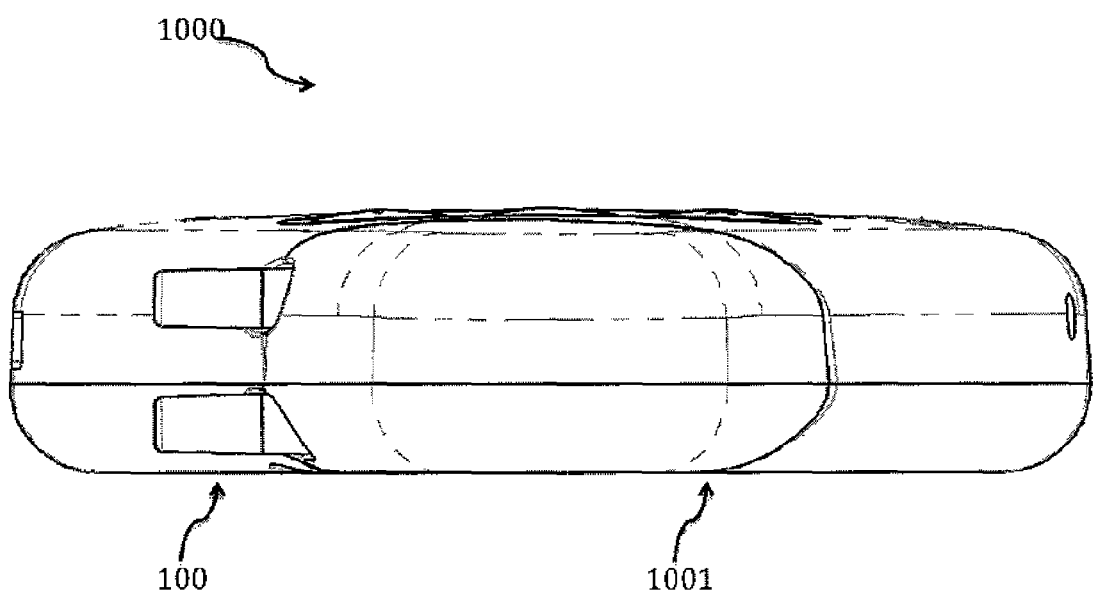

In another embodiment of the present invention, a system 900 is shown in FIG. 9A. Referring to FIG. 9A, in the system 900, the medicament can be filled in reservoirs 200a, 200b of a cartridge system 101 using an instrument, for example, a syringe 901. Referring to FIGS. 9B-9C, the cartridge system 101 has orifices 902a, 902b on the inlet/outlet members 700a, 700b which are in fluid connection with reservoirs 200a, 200b, respectively. Alternatively, the orifices 902a, 902b can be located on the reservoirs 200a, 200b.

Referring to FIGS. 10A-10D, a drug delivery device 1000 including a pump driver system 1001 and the cartridge system 100 is shown. The cartridge system 100 snaps into the pump driver system 1001 and is securely engaged to it. The pump driver system 1001 includes, among others, a driver, a controller, and a power source. The driver electromagnetically drives the magnets 500 that applies a force to the pump membrane 400 causing it to deflect resulting in precise volumetric delivery of the fluid medicament from the reservoirs 200a, 200b. The deflection of the pump membrane 400 results in a change of pressure within the chambers of the reservoirs 200a, 200b resulting in an outward flow of the fluid medicament contained within the reservoirs 200a, 200b. The force applied by the driver onto the pump membrane 400 can be adjusted using the controller. The drug delivery device 1000 can be powered by batteries, connected to a power outlet using an adapter, or other sources of power.

Figure 11:
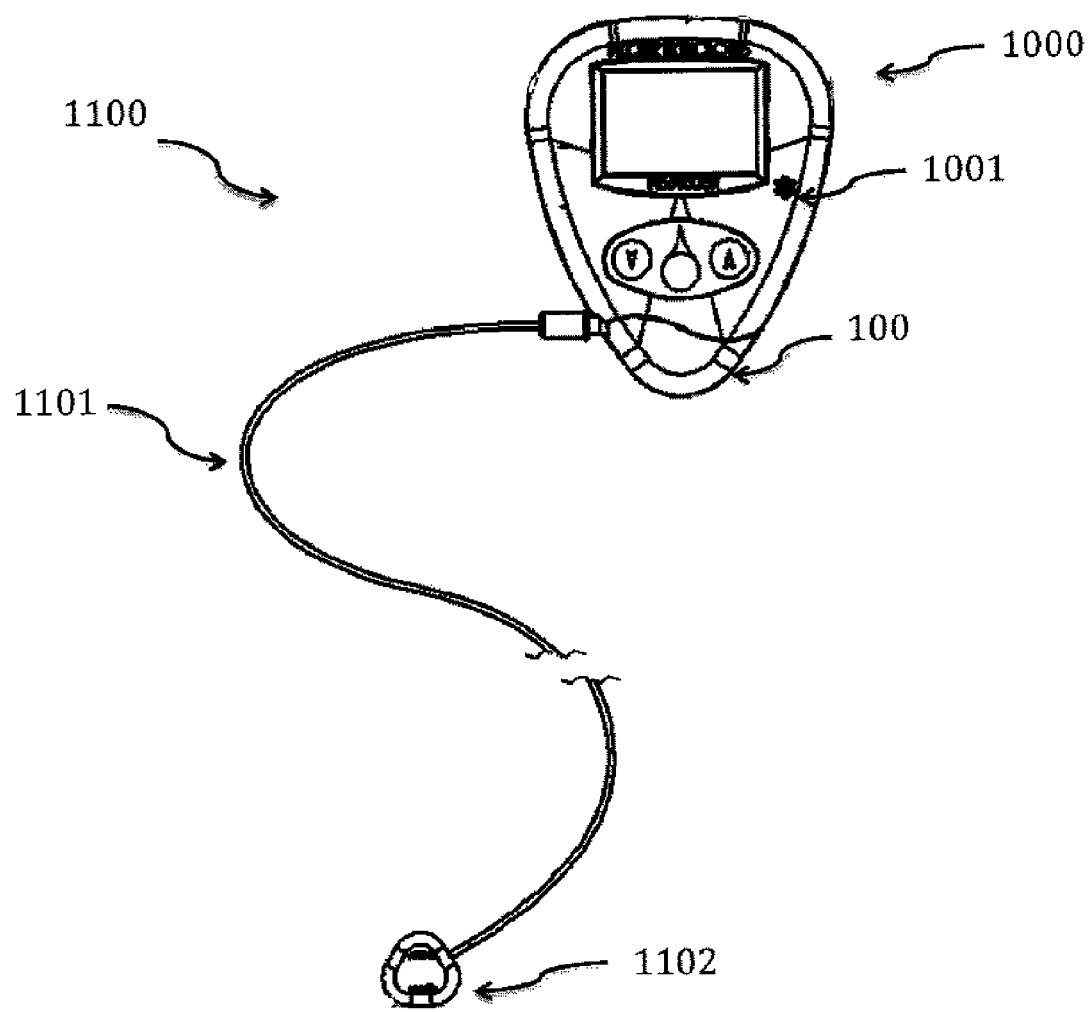
FIG. 11 illustrates the drug delivery device with accessories in accordance with an embodiment of the present invention.

Referring to FIG. 11, the drug delivery device 1000 with accessories 1101, 1102 is shown. A conduit 1101 for delivering the fluid medicament from the drug delivery 1000 is preferably, a single tube catheter or a Y-catheter. The distal end of the conduit 1101 is securely attached to a luer slip on the proximal end 701b of the fluid outlet component 701 of the inlet/outlet member 700a in the cartridge system 100. The proximal end of the conduit 1101 is securely engaged to a cannula and insertion mechanism 1102 including a sensor and a needle. When the drug delivery device 1000 uses two reservoirs 200a, 200b, the conduit is preferably a duel tube Y-catheter whose distal ends are securely attached to the luer slips on the proximal ends 701b of the fluid outlet component 701 of the inlet/outlet members 700a, 700b. The proximal end of the conduit 1101 is securely engaged to a cannula and insertion mechanism 1102 including a sensor and a needle whereby the two medicaments are mixed in the canola before entering the needle. In another method of delivering the medicament, the cannula and insertion mechanism 1102 has a plurality of needles and the medicaments are delivered through separate needles.

A diabetic patient can use the drug delivery device 1000 along with the accessories 1101, 1102 shown in FIG. 11. In a method of delivering medicament using a drug delivery device 1000, a drug delivery device 1000 having a pump driver system 1001 and a cartridge system 100 is provided to the patient user. A plurality of pre-filled reservoirs 200a, 200b containing fluid medicaments are loaded to the cartridge system 100. The cartridge system 100 is then snapped into and securely engaged to the pump driver system 1001. The user then selects various parameters on a user interface on the pump driver system 1001. These parameters can include, but not be limited to, basal rate, insulin amount, bolus rate based on the calories of carbohydrates, protein, fat or fiber consumed, and the blood glucose level including the actual and target glucose levels. The user can either select pre-determined values or specify user-defined values for each of the parameters. The user connects an infusion set having accessories 1101, 1102 to the drug delivery device 1000.

The step of connecting an infusion set to the drug delivery device can include connecting the distal ends of a Y-catheter to the luer slips of the fluid outlet component of the inlet/outlet members. Subsequently, the patient user can place an inset of the infusion set on a body part of the patient, attach the infusion set to the body, and switch on the drug delivery device. When the patient user uses only one reservoir in the cartridge system, the step of connecting an infusion set to the drug delivery device can include connecting the distal end of the Y-catheter to the luer slip of the outlet component of the inlet/outlet member.

The delivery of medicaments can be at a controlled and continuous rate for a pre-determined or user-defined period of time. Alternatively, the delivery of medicament can also be at a programmable rate that is regulated by the patient. The drug delivery device can be preprogrammed to infuse medicaments at a constant basal rate or variable bolus rate over a certain period of time. The device can deliver micro-doses of medicaments—insulin, glucagon or other medication—at controlled and continuous rate for a pre-determined period of time.

In another method of delivering medicament using the drug delivery device 1000 having the cartridge system 100, a drug delivery device 1000 having a pump driver system 1001 and a cartridge system 100 is provided to the patient user. A plurality of reservoirs 200a, 200b are loaded to the cartridge system 100 and the reservoirs 200a, 200b are filled with medicaments using an instruments, for example, a syringe. The cartridge system 100 is then snapped into and securely engaged to the pump driver system 1001. The user then selects various parameters on a user interface on the pump driver system 1001. These parameters can include, but not be limited to, basal rate, insulin amount, bolus rate based on the calories of carbohydrates, protein, fat or fiber consumed, and the blood glucose level including the actual and target glucose levels. The user can either select pre-determined values or specify user-defined values for each of the parameters. The user connects an infusion set having accessories 1101, 1102 to the drug delivery device 1000. Subsequently, the patient user can place an inset of the infusion set on a body part of the patient, attach the infusion set to the body, and switch on the drug delivery device.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

The invention claimed is:

1. A cartridge system, comprising:
    a first reservoir;
    a second reservoir;
        a first pump body insert comprising:
            a first fluid receiving opening,
            a first fluid discharge opening,
            a plurality of first pump body insert channels configured to direct a first flow of fluid from the first fluid receiving opening through the first fluid discharge opening;
        a second pump body insert comprising:
            a second fluid receiving opening,
            a second fluid discharge opening,
            a plurality of second pump body insert channels configured to direct a second flow of fluid from the second fluid receiving opening through the second fluid discharge opening;
    a pump membrane positioned between the first pump body insert and the second pump body insert, wherein the plurality of first pump body insert channels and the plurality of second pump body insert channels provide pump membrane support and limit deformation and reverse flow of fluid; and
    a plurality of magnets associated with the pump membrane and configured to apply a magnetic force to the pump membrane,
    wherein the first pump body insert is in fluid communication with the first reservoir, and
    wherein the second pump body insert is in fluid communication with the second reservoir, and
    wherein the pump membrane moves according to the magnetic force applied.

2. The cartridge system of claim 1, wherein a first magnet of the plurality of magnets is located adjacent a first side of the pump membrane, and wherein a second magnet of the plurality of magnets is located adjacent a second side of the pump membrane.

3. The cartridge system of claim 1, wherein the plurality of magnets includes a first magnet and a second magnet, wherein the first magnet is located adjacent a first side of the pump membrane, wherein the second magnet is located adjacent a second side of the pump membrane, and wherein the pump membrane deflects according to the magnetic force applied.

4. The cartridge system of claim 1, wherein the pump membrane is pre-stressed.

5. The cartridge system of claim 1, further comprising a plurality of valve membranes.

6. The cartridge system of claim 1, further comprising a first inlet/outlet member in fluid communication with the first reservoir and the first pump body insert and a second inlet/outlet member in fluid communication with the second reservoir and the second pump body insert.

7. The cartridge system of claim 6, further comprising a first valve membrane located at a region where the first pump body insert fluidly communicates with the first inlet/outlet member and a second valve membrane located at a region where the second pump body insert fluidly communicates with the second inlet/outlet member.

8. The cartridge system of claim 1, wherein the first reservoir contains a first fluid medicament and the second reservoir contains a second fluid medicament.

9. The cartridge system of claim 1, wherein the first reservoir and the second reservoir are substantially symmetrical, and wherein the first pump body insert and the second pump body insert are substantially symmetrical.

10. A cartridge system, comprising:
a first reservoir;
a second reservoir;
a first inlet/outlet member in fluid communication with the first reservoir;
a second inlet/outlet member in fluid communication with the second reservoir;
a first pump body insert in fluid communication with the first inlet/outlet member, wherein the first pump body comprises:
　a first fluid receiving opening,
　a first fluid discharge opening,
a plurality of first pump body insert channels configured to direct a first flow of fluid from the first fluid receiving opening through the first fluid discharge opening;
a second pump body insert in fluid communication with the second inlet/outlet member, wherein the second pump body comprises:
　a second fluid receiving opening,
　a second fluid discharge opening,
a plurality of second pump body insert channels configured to direct a second flow of fluid from the second fluid receiving opening through the second fluid discharge opening;
a pump membrane positioned between the first pump body insert and the second pump body insert; and
a plurality of magnets adjacent the pump membrane.

11. The cartridge system of claim 10, further comprising a first valve membrane and a second valve membrane, wherein the first valve membrane is located at a region where the first pump body insert fluidly communicates with the first inlet/outlet member, and the second valve membrane is located at a region where the second pump body insert fluidly communicates with the second inlet/outlet member.

12. The cartridge system of claim 10, wherein a first magnet of the plurality of magnets is located adjacent a first side of the pump membrane, wherein a second magnet of the plurality of magnets is located adjacent a second side of the pump membrane, and wherein the pump membrane deflects in response to a magnetic force applied by the first magnet and the second magnet.

13. The cartridge system of claim 10, wherein the pump membrane is pre-stressed.

14. The cartridge system of claim 10, wherein the first reservoir contains a first fluid medicament and the second reservoir contains a second fluid medicament.

\* \* \* \* \*